US010247729B2

(12) United States Patent
Lee et al.

(10) Patent No.: US 10,247,729 B2
(45) Date of Patent: Apr. 2, 2019

(54) MEDIA ELABORATED WITH NEWLY SYNTHESIZED ANTIBODIES (MENSA) AND USES THEREOF

(71) Applicant: MICROBPLEX, INC., Atlanta, GA (US)

(72) Inventors: Frances Eun-Hyung Lee, Atlanta, GA (US); John L. Daiss, Rochester, NY (US)

(73) Assignee: MICROBPLEX, INC., Atlanta, GA (US)

( * ) Notice: Subject to any disclaimer, the term of this patent is extended or adjusted under 35 U.S.C. 154(b) by 402 days.

(21) Appl. No.: 14/704,429

(22) Filed: May 5, 2015

(65) Prior Publication Data

US 2016/0077094 A1 Mar. 17, 2016

Related U.S. Application Data

(60) Provisional application No. 61/988,517, filed on May 5, 2014.

(51) Int. Cl.
```
G01N 33/569    (2006.01)
G01N 33/68     (2006.01)
A61K 39/00     (2006.01)
```

(52) U.S. Cl.
CPC ... *G01N 33/56972* (2013.01); *G01N 33/6854* (2013.01); *A61K 2039/6037* (2013.01); *C12N 2760/16134* (2013.01); *C12N 2760/16234* (2013.01); *C12N 2760/18534* (2013.01); *G01N 2469/10* (2013.01); *Y02A 50/52* (2018.01); *Y02A 50/53* (2018.01); *Y02A 50/59* (2018.01); *Y02A 50/60* (2018.01)

(58) Field of Classification Search
CPC ......... G01N 33/56972; G01N 33/6854; G01N 2469/10; Y02A 50/52; Y02A 50/53; Y02A 50/59; Y02A 50/60; A61K 2039/6037; C12N 2760/16134; C12N 2760/16234; C12N 2760/18534
See application file for complete search history.

(56) References Cited

U.S. PATENT DOCUMENTS

2010/0279352 A1*  11/2010  Ahmed ............... C07K 16/00
                                                     435/69.6
2011/0229914 A1*  9/2011   Lee ................. G01N 33/56911
                                                     435/7.92

FOREIGN PATENT DOCUMENTS

WO      2007003041 A1      1/2007
WO   WO 2009/035738 A2     3/2009

OTHER PUBLICATIONS

Halliley et al., "Peak frequencies of circulating human influenza-specific antibody ..." Vaccine, Elsevier Ltd, GB, vol. 28, No. 20, Apr. 2010, 6 pages.
Kyu et al., "Frequencies of human influenza-specific antibody secreting cells or plasmablasts ..." Journal of Immunological Methods, vol. 340, No. 1, Jan. 2009, 6 pages.
He et al., "Plasmablast-derived polyclonal antibody response ..." Journal of Immunological Methods, vol. 365, No. 1, Dec. 2010, 9 pages.

(Continued)

*Primary Examiner* — Gailene Gabel
(74) *Attorney, Agent, or Firm* — Meunier Carlin & Curfman LLC

(57) ABSTRACT

Disclosed are methods and kits for early detection of antigen exposure through the presence or absence of antigen-specific antibodies.

7 Claims, 24 Drawing Sheets

(56) References Cited

OTHER PUBLICATIONS

Lee et al., "Novel Method for Diagnosing Microbial Infections . . . " retrieved from the internet: www.atsjournals.org/doi/abs/10.1164/ajrccm-conference.2010; Jan. 2010, 1 page.
Czerkinsky et al., "A Solid-Phase Enzyme-Linked Immunospot (ELISPOT) Assay for Enumeration . . . " Journal of Immunological Methods, vol. 65, No. 1-2, Dec. 1983, 13 pages.
Extended European Search Report released by the European Patent Office dated Oct. 2, 2015, 10 pages.
Communication Pursuant to Article 94(3) EPC, issued in European Application No. 15166489.3, dated Sep. 29, 2016.

\* cited by examiner

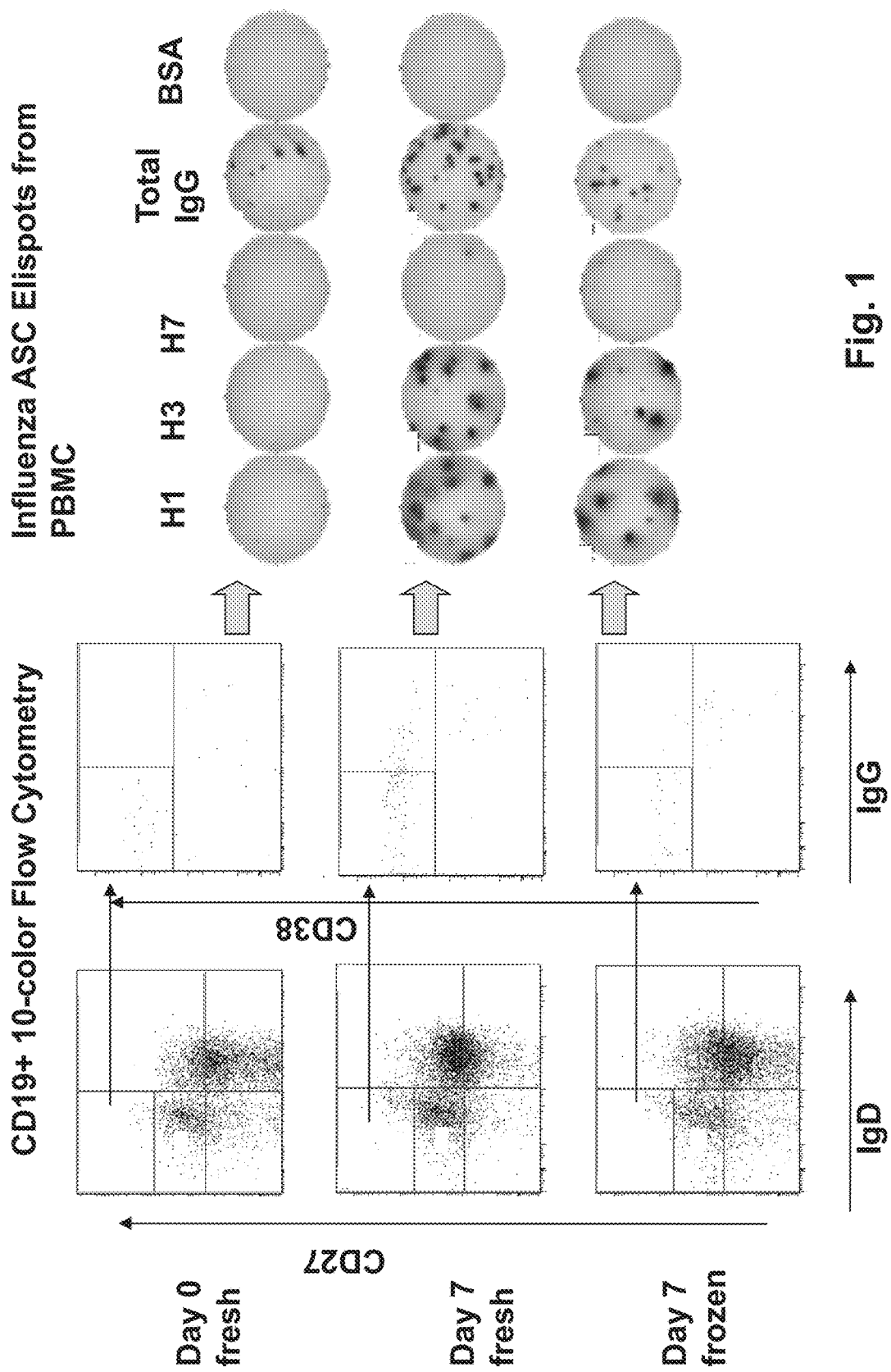

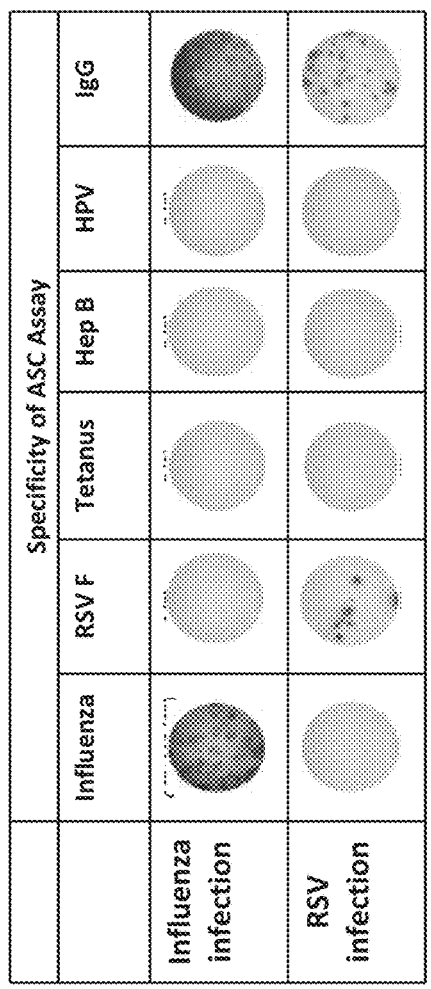
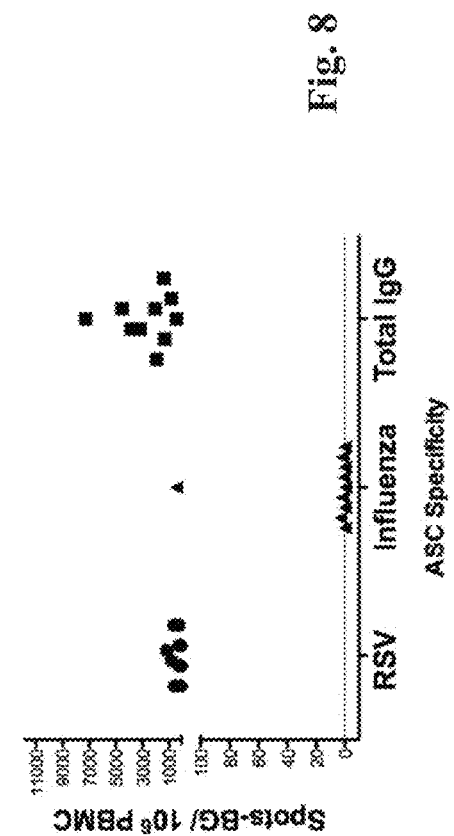
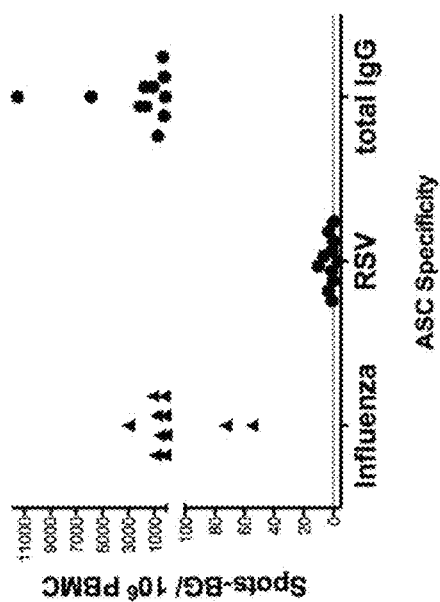
Fig. 8

MEDIA ELABORATED WITH NEWLY SYNTHESIZED ANTIBODIES (MENSA) AND USES THEREOF

This application claims the benefit of U.S. Provisional Application No. 61/988,517, filed on May 5, 2014, which is incorporated herein by reference in its entirety.

This invention was made with government support under AI050029 awarded by the National Institutes of Health. The Government has certain rights in the invention.

I. BACKGROUND

Current methods of assessing antibody mediated vaccine responses are used to measure rises in pre and post exposure antibody titers (i.e., neutralizing antibodies via ELISA). Though effective, the current methods necessitate a waiting period of approximately 30 days post antigen exposure before an assessment for efficacy can be made.

Similarly, while the presence of antibodies specific to an antigen can be used to determine antigenic exposure, a delay of 30 days post exposure creates a significant hurdle in the ability to provide a diagnosis to antigen exposure and delay treatment. In the event of an acute infectious disease, the disease will often have run its course before a diagnosis could be made using current methodology. Rapid diagnosis is even more essential in the event of a bioterrorism attack for containment and treatment of infected persons; situations where it is also essential to inform decisions to "shut down" major cities or ground all air travel which carry tremendous social, political and economic implications. Yet, current diagnostic methods are rooted in microbe identification and only work in a very restricted time window.

Moreover, plasma antibodies also suffer from many limitations as these tests are unable to distinguish newly proliferated antibodies from pre-existing circulating antibodies. Thus single samples may not reflect recent exposure and accurate diagnosis is delayed and complicated by the need of acute and convalescent samples. Further complicating matters is that current methodologies can require as much as 24 hours to perform, need specialized machinery not necessarily present in clinical laboratories, and need high trained technicians to perform. What is needed are new rapid highly specific and sensitive methods of antibody detection that can distinguish newly created antibodies from preexisting antibodies, and can reduce the level of skill needed to perform the task.

II. SUMMARY

In one aspect, disclosed herein are analytical matrixes comprising media elaborated with newly synthesized antibodies (MENSA) from recently proliferated antibody secreting cells (ASC) circulating in the blood; wherein the analytical matrix comprises at least a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or peripheral blood mononuclear cells (PBMC).

Disclosed are methods and kits related to assessing the level or presence or antibody secreting cells (ASC) in a subject following antigen exposure. In one aspect, the disclosed methods and kits can distinguish ASC or antibodies derived from recent antigenic exposure from pre-existing ASC.

In another aspect, disclosed herein are methods of detecting recent antigenic exposure of a subject comprising obtaining newly proliferated ASC from the subject between 3 and 45 days following antigenic exposure or during viral shedding, separating the plasma from the newly proliferated ASC, and measuring the number of newly proliferated ASC or antibodies from the newly proliferated ASC, wherein the presence of ASC or antibodies specific for an antigen indicates recent antigenic exposure.

In another aspect, disclosed herein are methods of diagnosing a subject comprising obtaining whole blood or PBMC from the subject between 3 and 45 days following antigenic exposure or during viral shedding, separating the plasma from the newly proliferated ASC, and measuring the number of newly proliferated ASC or antibodies from the newly proliferated ASC on a disease panel, wherein the presence of ASC or antibodies specific for an antigen on a panel indicates the subject as an ongoing infection with the source of the antigen.

In another aspect, disclosed are methods of assessing the efficacy of a vaccine in a subject comprising obtaining peripheral blood mononuclear cells (PBMC) from the subject between 3 and 45 days following administration of the vaccine, measuring the number of antibody secreting cells (ASC) in the PBMC, and comparing the number of ASC to a standard, wherein more ASC in the PBMC relative to a standard indicates an efficacious vaccine.

In another aspect disclosed are methods of assessing the need of the administration of a booster immunization in a subject comprising obtaining whole blood or peripheral blood mononuclear cells (PBMC) from the subject between 3 and 45 days following administration of a vaccine, separating plasma from the newly proliferated ASC, washing the newly proliferated ASC, culturing the newly proliferated ASC in media conducive to antibody production and expression (MENSA), measuring the number of antibody secreting cells (ASC) in the PBMC, and comparing the number of ASC to a standard, wherein fewer ASC in the PBMC relative to a standard indicates the need for an immunization boost.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows a comparison of fresh vs. frozen plasmablasts by flow cytometry and ASC ELISPOTS pre- and 7 day post-influenza vaccination.

FIGS. 2A, 2B, 2C, and 2D show influenza-specific ASC from fresh PBMC Pre- and 7 day-post vaccination. P=one tailed paired T-test FIGS. 3A, 3B, 3C, and 3D show a comparison of ASC from fresh vs. frozen PBMC 7 day post-influenza vaccination. R=correlation coefficients.

FIGS. 4A and 4B show the kinetics of influenza-specific ASC (plasmablasts) in peripheral blood from 2 young healthy subjects. FIG. 4A shows a patient with prior influenza vaccination exposure through a history of annual influenza vaccinations. FIG. 4B shows a patient with no history of prior vaccination or infection.

FIG. 5 shows antigen-specific ASC ex vivo in the blood after antigen exposure is short-lived approximately from day 5-15 after a single antigen dose. Shown in FIG. 5 is a representative of the kinetics of one subject's ASC for total IgG, Hemaglutinins H1, H3, H7, trivalent influenza vaccine (TIV) from 2006 directly ex vivo from the blood pre and days post-TIV. Each circle represents wells coated with either total anti-human IgG, purified H1 (New Caladonia), H3 (H3 A/Wyoming, which is closely related to A/Wisconsin), H7 (an avian strain to function as a negative control), and TIV (TIV vaccine components are H1 A/New Caledonia/20/99, He A/Wisconsin/67/2005, and B/Malaysia/2506/2004). PBMC numbers 30,000 or 300,000 were added to each well as shown above and incubated for 18-20 hours. Cells were removed and biotinylated anti-human IgG (recognizing all 4 subclasses) was added and developed. The total IgG ASC frequencies can increase to 0.02-0.8% of the PBMC. The antigen-specific ASC frequencies of the total IgG can range from 20-60%.

FIGS. 6A, 6B, 6C, 6D, 6E, and 6F show the kinetics of 6 young healthy adult human subjects (subjects 3-8, panels 6A-6F, respectively) receiving influenza vaccine.

FIG. 7 shows antigen-specific ASC Elispots can further identify acute influenza infections of different influenza strains.

FIG. 8 shows the specificity of the microBspot™ assay. Blood samples were obtained from patients with influenza or RSV infections and the specificity of the antibodies to the assay assessed. FIG. 8A shows a typical response for patients with influenza or RSV and cross-reactivity against a panel of antigens. FIGS. 8B and 8C show the specificity of response to RSV or influenza across the entire spectrum of patients.

Figure 12:
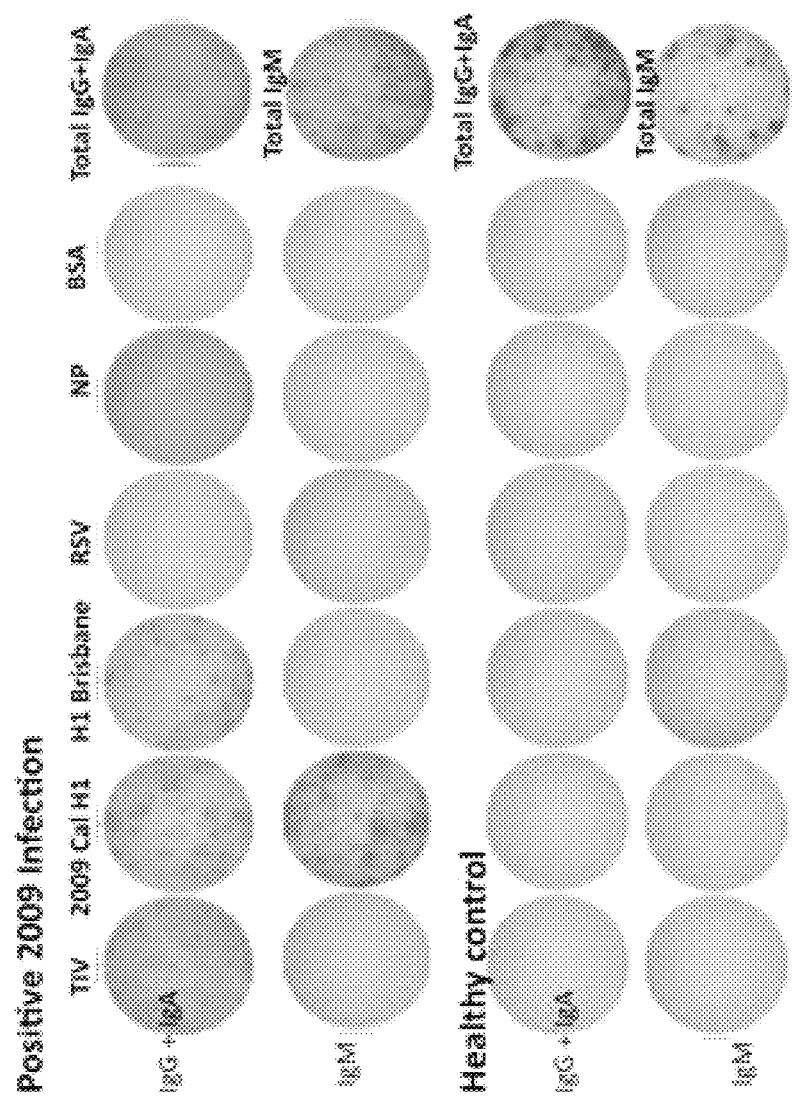

FIG. 12 shows Detection of IgG, IgA, & IgM influenza-specific antibodies by ASC Elispots in the blood of a patient on day 13 of illness (top 2 panels) and a non-infected adult control subject (bottom 2 panels). Antibody secreted by total, un-stimulated PBMC were tested in an ELISPOT based assay for binding to: TIV 2009-10, 2009 pandemic H1 (California 2009), seasonal H1 (Brisbane 2007), RSV F protein (un-related respiratory viral antigen), nucleoprotein from influenza A (NPA), and negative control of bovine serum albumin (BSA). 1st & 3rd rows with combined IgG and IgA (IgG+IgA) ASCs from 30,000 and 300,000 PBMC from the patient & control. 2nd & 4th rows with IgM-ASCs from 300,000 PBMC. The right most column shows production of total IgG+IgA or IgM ASCs as labeled.

Figure 13:
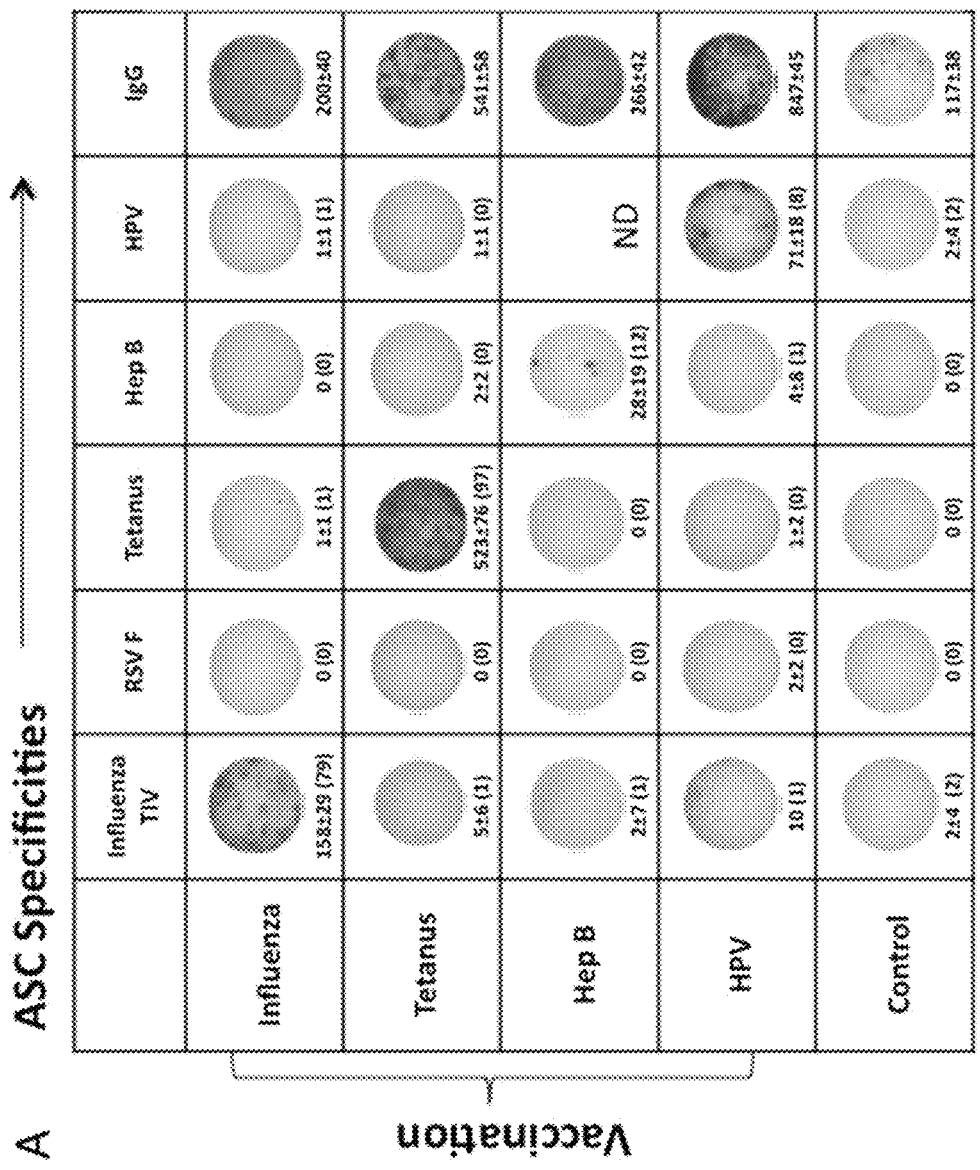

FIG. 13 shows High specificity of the ASC ELISPOT assay is consistently detected in subjects after immunization for the corresponding Ags with the absence of cross-reactivity to nonspecific pathogens. For these experiments, ASC ELISPOT assays were performed directly ex vivo without in vitro proliferation. A, Representative wells of the ELISPOT assay. The sample in each row is representative blood from four subjects with indicated vaccination. Bottom row is representative of an asymptomatic healthy subject at steady state. Columns represent ASC assays specific for the following Ags: TIV, RSV F, tetanus toxoid (Tet), hepatitis B vaccine, and HPV vaccine. PBLs (PBMCs) were incubated at 300,000 cells/well directly ex vivo (without stimulation). Spots were detected with anti-human IgG. Total IgG ASCs are shown in the far right column. Numbers below each well represent mean 6 SD of triplicate wells. Numbers in parentheses indicate percentage of Ag-specific to total IgG spots.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular antigen or antibody is disclosed and discussed and a number of modifications that can be made to a number of molecules including the antigen or antibody are discussed, specifically contemplated is each and every combination and permutation of antigen or antibody and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

MENSA

Following antigen exposure from vaccination or infection, naïve and/or memory B cells proliferate and differentiate into ASCs in lymph nodes. These ASCs are thought to be generated in activated lymph nodes, a compartment that is difficult to sample. These recently blasted ASCs leave the lymph node and burst into the circulation as they migrate to other tissue sites such as the bone marrow, spleen, or sites of inflammation presumably reflecting the migration of these effector cells to survival niches in the bone marrow and spleen. These highly informative cells are readily detectable from as little as 1-5 cc of blood and in the absence of measurable bystander effect on unrelated antigenic specificities. As opposed to historic plasma antibodies produced by resident bone marrow plasma cells, newly synthesized antibodies reflect an ongoing immune response as they are secreted from newly proliferated antibody secreting cells (ASC) that burst dramatically in the peripheral blood just a few days after acute infections and can persist in the circulation for several weeks.

In one aspect, disclosed herein is a novel analytical matrix for determining antigenic exposure referred to herein as MENSA. MENSA (Media containing ASC-Elaborated Newly Synthesized Antibodies or MEdia of Newly Synthesized Antibodies) comprises "newly synthesized antibodies" directly elaborated from specialized cells during acute illness or following vaccination. MENSA differs from plasma in that the antibodies present in plasma are from long-lived plasma cells in the bone marrow and not newly syntheized antibodies. MENSA also differs from media containing PBMC in that there are no memory B cells present and the ASC therein are secreting new synthesized antibody specific for an ongoing antigenic insult. Thus, put another way, disclosed herein is media substantially free of pre-existing antibody, but comprising newly synthesized antibodies from recently proliferating ASC in the blood. Accordingly, MENSA further differs from plasma antibody in that the antibody to MENSA, being essentially free of pre-existing antibody, is directed to a single antigen or foreign substance or organism; whereas, plasma antibody has antibodies specific to every prior antigenic experience. Moreover, MENSA is not merely isolated natural antibody or ASC but a mixture of media and at a minimum newly synthesized antibodies grown in culture in the absence of contaminating plasma antibodies and in that through the creation of the analytical matrix a properties and functions are gained such as the absence of pre-existing antibodies, the ability to detect recent antigenic or ongoing antigenic exposure; non of which can be accomplished with antibodies directly removed from a subject.

It is understood and herein contemplated that "media substantially free of pre-existing antibody," refers to media where the amount of contaminating pre-existing plasma antibodies in the media is reduced at least 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold relative to whole blood, plasma, or PBMC of the biological sample from which the newly proliferating ASC were obtained. Alternatively, the "media substantially free of pre-existing antibody," can refer to media where any contaminating pre-existing plasma antibody has been reduced at least 0.76-3.90 mg/dL when the contaminating pre-existing plasma antibody is IgA; at least 6.50-15.00 mg/dL when the contaminating pre-existing plasma antibody is IgG; or at least 0.40-3.45 mg/dL when the contaminating pre-existing plasma antibody is IgM. Where the specific IgG subclass is IgG1 the contaminating pre-existing plasma antibody can be reduced at least 3.41-8.94 mg/dL. Where the specific IgG subclass is IgG2 the contaminating pre-existing plasma antibody can be reduced at least 1.71-6.32 mg/dL. Where the specific IgG subclass is IgG3 the contaminating pre-existing plasma antibody can be reduced at least 0.184-1.060 mg/dL. Where the specific IgG subclass is IgG4 the contaminating pre-existing plasma antibody can be reduced at least 0.024-1.210 mg/dL. Put another way, in one aspect, disclosed herein are analytical matrixes comprising media elaborated with newly synthesized antibodies (MENSA) from recently proliferated antibody secreting cells (ASC) circulating in the blood; wherein the analytical matrix comprises at least a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or peripheral blood mononuclear cells (PBMC). It is understood and herein contemplated that the reduction of contaminating plasma antibodies, plasma cells, and in some cases neutrophils and red blood cells is an important aspect of the disclosed methods and failure to sufficiently remove the contaminants will affect the ability to perform the disclosed methods and obtain a reliable result. In one aspect, where reduction of contaminating pre-existing plasma antibodies is claimed or discussed it is further contemplated a contemporaneous reduction in other contaminants such as red blood cells, plasma cells, neutrophils, and/or B cells.

MENSA can function as a new serologic surrogate with similarly high specificities of antibodies, but with several major advantages. First, the pathogen-specific ASCs require only a single time point and can identify patients during the acute illness. Since the "historic or old" contaminating antibodies found in plasma are removed and only the newly synthesized antibodies measured from newly proliferated ASC, only antibodies or immune reactions to the current illness are measured. Another advantage of measuring MENSA over insensitive low affinity IgM measurements is reliability. MENSA can detect all antibody isotypes such as high affinity IgG or IgA as well as low affinity IgM antibodies which can increase its reliability. Herein is shown that the following characteristics of MENSA as measured by ASC Elispots: (1) high pathogen-specificity with no bystander effect (2) specificity only during acute illness and not during asymptomatic periods 1 (3) detection at the time of initial clinical presentation. Third, MENSA is free from substances that interfere with clinical assays including but not limited to pharmaceutical agents and non-pharmaceutical drugs, lipemia, icterus, bile salts, hemoglobin, heterophilic antibodies, autoimmune antibodies, vitamins, antioxidants, and nutritional supplements. Fourth, in some aspects, it is contemplated that MENSA can be cell free comprising antibodies and media which provides for compatibility with a large number of immune-analytical readouts that do not work with non-cell free samples.

The appearance of re-assorted viruses with either avian or swine components poses a continuous pandemic threat of potentially dire consequences, and pneumonia and seasonal influenza virus (P & I) consistently rank as the 4th most common discharge diagnosis. As a recently emerging pathogen, the 2009 pandemic H1N1 influenza virus required accurate diagnostic testing for clinical decision making, rapid patient isolation, as well as understanding the morbidity and mortality of the disease.

In 2009-2010, 41-84 million cases of H1N1 influenza virus infection occurred in the US by CDC estimates, and H1N1 related hospitalizations ranged from 183,000 to 378,000 with death estimates between 8,330 to 17,160. These numbers are underestimates of the true influenza disease burden since early in pandemic, diagnosis was quite limited due to limited availability of testing in specialized government (state department of health) facilities. In addition, during the height of the pandemic, only a handful of large hospitals had capacity to perform PCR tests to confirm 2009 H1N1 infections. Clearly, diagnostic tests with wide accessibility using existing hospital instrumentation would have been extremely advantageous and valuable during the 2009 influenza pandemic.

Like seasonal infections, elderly individuals were prominent among susceptible populations prior to 2009. However, during this pandemic, demographics of the at risk population included children, young adults (even those with previous history of seasonal influenza virus infections), pregnant and postpartum mothers, and patients with obesity, diabetes mellitus, COPD and asthma. Unfortunately, previous history of influenza infection and/or compliance with annual influenza vaccine did not insure protection from the new re-assorted strains of influenza virus leaving many populations vulnerable.

Treatment for influenza infection includes anti-viral agents amantadines, and neuraminidase inhibitors, oseltamivir, zanamivir, 41 and peramivir (for emergency use authorization, and due to emergent reports of oseltamivir-resistant viruses, judicious use of these neuraminidase inhibitors was recommended for only severely ill patients.

Yet, post-pandemic studies showed that early treatment with antiviral agents reduced the duration of hospitalization and the risk of progression to severe disease requiring ICU admission or death. Lessons from this past pandemic illustrate the importance for better diagnostic tests that can be rapidly adapted and widely available for newly emerging pathogens to save lives. Current influenza virus diagnostic tests include PCR or viral antigen detection which are helpful only when the patient is shedding virus (category of microbe detection and not the host immune response). In previously healthy adults, this viral isolation window is limited to a few days after symptom onset. Optimal result for RT-PCR is at the time of highest viral load which typically occur when patients are studied within 48 hours of symptom onset. Unfortunately, only a fraction of patients with influenza-like-illness (ILI) will present to a health care provider within 2 days of illness, and previously healthy patients with severe disease are likely to present much later thereby diminishing significantly the performance of RT-PCR assays in clinical practice. In keeping with this observation, serological assays significantly outperformed PCR in a paired study of 33 Intensive Care Unit admissions at the peak of the 2009 winter season. It showed that PCR assays missed one-third of the cases that were identified by serology. This study illustrates the limitations of RT-PCR assays and highlights the superior sensitivity of serological approaches which unfortunately contribute to diagnosis largely in a retrospective fashion. This is where a single-time diagnostic MENSA measurement could be life-saving.

Using research ASC Elispot, it was shown that ASC in MENSA secrete antibodies with high specificity for the offending antigen; can be detected early after infection; and, in contrast to microbe isolation test (such as PCR), can be detected for significantly longer periods of time. In fact, MENSA is the first immune biomarker to reliably produce results with antibody specificity at the time of acute illness. Also using ASC Elispot assays, it was shown herein that the novel analyte provides sensitivity and specificity of 93% and 100% in adult patients with acute respiratory viral infection (i.e. Respiratory Syncytial Virus, RSV). The data also demonstrate the very high specificity of this analyte for the diagnosis of influenza infections. Current research grade ASC Elispots show that measurement of newly synthesized antibodies represents a powerful and innovative class of diagnostic assays. This design validates this novel diagnostic approach and demonstrates easy adaptability to two different categories of bioterrorism agents, a live viral pathogen and a toxin.

To isolate the MENSA analyte, MENSA is separated from contaminating pre-existing antibody (typically present in the plasma) and other circulating plasma cell and B-cell populations. The separation of MENSA from the contaminating pre-existing antibody (typically present in the plasma) and other circulating plasma cell and B-cell populations can comprise any means known in the art including but not limited to magnetic bead cell sorting, FACS, and ficoll gradient separation. Moreover, the methodology used to separate the plasma from the newly proliferated ASC can actively separate either component so long as the end result is the removal of contaminating pre-existing antibody (and other circulating plasma cell and B-cell populations from the newly proliferated ASC. For example, the methodology could seek to remove plasma from the ASC such as a ficoll gradient and washing. Alternatively, the methodology could use markers on ASC for use on a column, filter, or sorting mechanism. Thus, it is understood and herein contemplated that whether any method disclosed herein recites that plasma is separated from the ASC or the ASC are separated from the plasma, there is no implied target of separation. Merely, what is meant is that resulting ASC will be free of plasma or B cell contaminant. When performed, the resulting analyte can comprise 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC.

A major candidate to improve the separation step is to capture the newly proliferated ASCs using magnetic beads bearing one, two, three, four, five, six, or more antibodies specific for cell surface markers unique to ASCs, specifically CD19, CD138, CD27, IgD, Ki67, and/or CD38. One or more of CD19, CD138, CD27, IgD, Ki67, and/or CD38 can also be used in FACS sorting of the newly proliferated ASC.

Whole blood and PBMC CD19+ isolation was less efficient than density purified CD38+ enriched selections for both total IgG and influenza-specific ASC frequencies per mL of blood. This result is not surprising since CD19 expression can be slightly lower on ASC than naïve and memory B cells even though circulating ASCs have both CD19 and CD38 cell surface expression. Therefore, a custom blended panel of bead marker sets can be used which includes CD19 and CD38 and others including but not limited to CD138, CD27, IgD, and Ki67 to optimally isolate the circulating ASC fraction from whole blood. These commercially available bead isolation steps typically require magnetic bead-laden ASCs that are retained by a magnet while the remainder of the blood cells and plasma are washed away. Thus, in one aspect disclosed herein are methods of isolating MENSA comprising obtaining whole blood, or PBMC from a subject, separating the newly proliferated ASC from the plasma, washing the newly proliferated ASC, and incubating the newly proliferated ASC in a media that supports maintenance of ASC and antibody secretion. It is understood and herein contemplated that the disclosed method will result in a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC.

As used throughout this application, the term "washing" refers to a process of removing contaminants such as plasma, PBMC, whole blood, and pre-existing antibodies from population of cells of interest, such as, for example newly proliferated ASC. It is understood and herein contemplated that washing comprises the administration of an excess volume washing solution to dilute any contaminants. It is understood that washing can comprise a means for separating the newly proliferated ASC from the excess washing solution such as, for example, centrifugation (also referred to as spinning). The washing solution can then be discarded and washed cells re-suspended in a suitable media. In one aspect the wash solution can comprise any media suitable for said purpose including but not limited saline, buffered saline, and tissue culture media such as, for example MEM, DMEM, RPMI, Media 199, Opti-MEM, F10, Ham's F12, IMDM, each with or without serum, such as, Fetal Calf serum or Fetal Bovine serum. It is further understood that a rinse and spin wash cycle can be performed more than one time each time decreasing the contaminants and increasing the purity of the newly proliferated ASC. For example, the rinse and centrifugation cycle can be performed one, two, three, four, five, six, seven, eight, nine, ten, or more times. It is further understood that through washing, the purity of the sample can comprise at least a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC. Accordingly, in one aspect, disclosed herein are method of isolating MENSA comprising obtaining whole blood or PBMC from a subject, separating plasma from the newly proliferated ASC obtained from the whole blood or PBMC, washing the newly proliferated ASC, and incubating the newly proliferated ASC in a media that supports maintenance of ASC and antibody secretion, wherein the washed ASC comprise at least a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC.

It is understood and herein contemplated that there are many mechanisms that can be used to separate the newly proliferated ASC from plasma. For example, ASC can be separated using ficoll gradients, elutriation, cell sorting methods such as magnetic bead sorting or fluorescence acquired cell sorting (FACS). While careful multicolor flow cytometry can identify several distinct subsets of circulating ASC populations, the majority of these cells can be captured within the CD19+, CD27hi, CD38hi population containing >90% of recently proliferated cells as indicated by the almost universal expression of the nuclear proliferation antigen Ki67. Accordingly, where ASC are sorted based using magnetic beads or fluorescence, the sort is based on the presence and/or absence of one or more surface markers to which a tagged antibody can be bound. Examples of cell surface markers for separating newly proliferated ASC include but are not limited to CD38, CD27, CD19, CD138, IgD, and Ki67. Thus, for example, in one aspect disclosed herein are methods of isolating MENSA comprising obtaining whole blood or PBMC from a subject, separating the plasma from the newly proliferated ASC using magnetic bead separation comprising one, two, three, four, five, or six or more of anti-CD38, anti-CD27, anti-CD19, anti-CD138, anti-IgD, or anti-Ki67 beads, and incubating the newly proliferated ASC in a media that supports maintenance of ASC and antibody secretion.

In order for MENSA to be useful for detection of antigenic exposure or for diagnosis, secreted antibodies that are newly synthesized in response to activation of ASC must be present and pre-existing antibodies should be absent. Thus, the media should comprise sugars and amino acids needed for protein synthesis, newly activated ASC, and at least a two, three, four, five, six, seven, eight, nine, or ten log reduction in plasma or serum from the subject. Additionally, MENSA may contain survival factors such as IL-2, IL-6, IL-15, IL-21, and IFN-α, APRIL, enhancers of antibody secretion such as IL-21, other non-antibody secreting cells such as T cells or macrophage, but not red blood cells. Also, depending on the ASC separation method employed, the MENSA may also contain magnetic beads or compounds needed for rapid separation of ASC from whole blood, PBMC, or plasma.

Methods of Use

In one aspect, disclosed herein are methods of determining antigenic exposure in or diagnosing a subject comprising obtaining MENSA, antibodies, antibody secreting cells (ASC) or peripheral blood mononuclear cells (PBMC) from the subject between 3 and 45 days following antigenic exposure or during viral shedding and detecting the presence and/or measuring the number of ASC or antibodies from the isolated ASC, wherein the presence of ASC or antibodies specific for an antigen indicates recent antigenic exposure to said antigen thereby diagnosing the subject with a disease. It is understood and herein contemplated that because the methods of determining antigenic exposure or diagnosing a subject comprise obtaining MENSA; it is contemplated that the methods specifically contemplate the additional steps for obtaining MENSA into the disclosed diagnostic or antigen exposure methods. Thus, in one aspect, disclosed herein are methods of diagnosing the presence of a disease or exposure to an antigen in a subject comprising obtaining whole blood, plasma, or PBMC from the subject between 3 and 45 days following antigenic exposure or during viral shedding; separating newly proliferated ASC from the plasma; washing the newly formed ASC, and measuring the number of newly proliferated ASC or antibodies from the newly proliferated ASC specific for an antigen; wherein the washed ASC comprise at least a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC; wherein the presence of ASC or antibodies specific for the antigen indicates the subject as an ongoing infection with the source of the antigen. It is further contemplated herein that the disclosed methods can further comprise incubating the newly proliferated ASC in a media that supports maintenance of ASC and antibody secretion following the washing step and prior to measuring the number of ASC.

It is understood and herein contemplated that it is possible that a sample may be obtained in one location and processed from diagnosis in a remote laboratory location or in a facility not to be performed by the individual who obtained the whole blood or PBMC for testing. Thus, in one aspect, disclosed herein are methods of diagnosis further comprising optional step of packaging and shipping the sample or part of the sample taken from the patient.

Prior to the disclosed methods, antigenic exposure was determined by serology, immunofluorescence, RT-PCR, or viral culture. Unfortunately, each of these methodologies has significant drawbacks that that make early rapid detection of antigenic exposure and diagnosis of a disease related to antigenic exposure in a clinical setting difficult at best. Specifically, viral culture had been used as the gold standard in the past; however, now the reference standard for diagnosis of influenza virus infection is RT-PCR or virus culture. In several small studies in patients with influenza-like illness (ILI), higher numbers of positives are detected by RT-PCR tests compared to culture. Since viral culture requires 3-14 days and is clinically impractical, it is no longer routinely used. In contrast, direct antigen detection can yield results in approximately 15 minutes; however, sensitivity is usually much lower ranging 50-70% with a specificity of 90%. More than 10 rapid influenza tests have been approved by the FDA, but during some influenza seasons, sensitivity can be much lower, as low as 27%. As recent as the 2009 H1N1 pandemic, sensitivity of the rapid antigen tests reached 45-51%, with results slightly better in infants under 2 years of age 107 because primary infection often leads to higher viral shedding.

Immunofluorescence microscopy with turnaround time of 1-4 hours can be used to confirm rapid influenza testing but its sensitivity and specificity rely on the presence of adequate number of infected cells which can vary.

RT-PCR is considered the most sensitive and specific of the diagnostic influenza assays since it does not require isolation of intact virus but can detect viral components. Primers that amplify the RNA encoding the relatively conserved influenza proteins (matrix or nucleoprotein) have been successful in detecting all viral strains to date. HA-specific RT-PCR can identify different influenza A virus subtypes but is not always performed. Sensitivity of RT-PCR is described as 100% compared to culture and may even exceed culture results by 5-15% since viral RNA may be detected days after live virus isolation. However, without a true gold standard, it is not known what the true sensitivity and specificity of PCR. Of note, one ICU study during the 2009 pandemic showed that PCR missed over 30% of the acute infections when compared to serology. This is indirect evidence that the sensitivity the technology disclosed herein is equal to or surpasses that of PCR for ICU patients.

Serology is useful when virus isolation is negative or inadequate and is the only available test using the host immune response. However, currently available immune assays preclude their routine use. IgM serology offers low diagnostic yields with frequent false positives, and a single IgG level is not helpful in diagnosing secondary respiratory infections in adults because they require longitudinal >>4-fold rises to determine a new infection. Unfortunately, serology has limited clinical utility and is only used for retrospective diagnosis since both an acute and convalescent sample is necessary. This limitation is particularly relevant to adults with history of multiple influenza infections in whom increases of strain specific antibody titers must be interpreted with caution. So, serology is helpful for epidemiological studies but is rarely used in clinical management.

With the exception of serology, all the above-mentioned tests involve viral detection; and therefore, sensitivity is greatly dependent on timing of specimen collection during the clinical phase. With regards the main current diagnostic approach, its usefulness is compromised by the correlation between the duration of viral shedding and the timing of clinical symptoms. In experimental influenza challenge models, symptoms develop 2-4 days after inoculation and peak viral shedding occurs prior to symptom onset with mean viral shedding (measured by PCR) ranging from 2.3-3.4 days depending on the virus type and subtype. Accordingly, in human disease, the optimal time for virus isolation tests is before the onset of symptoms.

By contrast, the presently described methods are the first in a category of reliable immunoassays at a single time point. The methods disclosed herein measure MENSA found in the blood only during the acute illness. The ASC Elispots used herein measure microbe-specific antibodies and not cytokines as known with commercially available IFNγ cytokine Elispot assays. While ASC Elispots are well established as a research tool, herein is the first to demonstrate the striking diagnostic potential of MENSA from circulating ASC. Accordingly, these methods are the first reliable rapid immune-based assay that yields high pathogen-specific diagnostic sensitivity and specificity at initial presentation thereby providing real-time information for treatment and quarantine decisions.

ASCs are circulating antibody-making cells that have been recently stimulated by ongoing infection. During an acute illness the total ASC increases to 2-20% of all B cells even though they constitute only <0.5% of B cell population in steady state. More importantly, 20 to 90% of ASCs are secreting antibodies specific for the infecting pathogen, resulting in a massive expansion of pathogen specific antibodies during illness. By isolating ASCs and measuring the secreted antibody products, two critical parameters are gained that make this technology superb for diagnostics. First, sensitivity is enhanced because the newly synthesized antibodies are relatively abundant and most are specific for the infecting pathogen. Second, specificity is improved by removing all of the contaminating pre-existing plasma antibodies among which are potentially confounding antibodies elicited by prior infections (from long-lived bone marrow resident plasma cells) and well-known interfering substances such as rheumatoid factor and heterophilic antibodies. This final elaboration fluid (MENSA) is a relatively "clean" which contains ONLY newly synthesized antibodies from the specialized ASC isolated from the blood.

Thus, in one aspect, disclosed herein are methods for assessing the level or detecting presence of antibody secreting cells (ASC) in a subject following antigen exposure comprising obtaining and isolating MENSA from the subject between 3 and 45 days following antigenic exposure or during viral shedding, and measuring the number of MENSA, wherein the presence of MENSA specific for an antigen indicates recent antigenic exposure. It is understood and herein contemplated that because the methods of assessing the level or detecting presence of antibody secreting cells (ASC) in a subject following antigen exposure comprises obtaining MENSA, it is contemplated that the methods specifically contemplate the additional steps for obtaining MENSA into the disclosed assessing the level or detecting presence of antibody secreting cells methods. Thus, in one aspect, disclosed herein are methods of detecting antigenic exposure or assessing the level of antigenic exposure in a subject following antigenic exposure comprising obtaining newly proliferated ASC from the subject between 3 and 45 days following antigenic exposure or during viral shedding, separating the plasma from the newly proliferated ASC, washing the newly proliferated ASC, incubating the newly proliferated ASC in a media that supports maintenance of ASC and antibody secretion, and measuring the number of antigen specific ASC or antibodies from the isolated newly proliferated ASC; wherein the washed ASC comprise at least a 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC; and wherein the presence of ASC or antibodies specific for an antigen indicates recent antigenic exposure and the number of ASC or antibodies specific for an antigen indicates the level of antigenic exposure. It is further contemplated herein that the disclosed methods can further comprise incubating the newly proliferated ASC in a media that supports maintenance of ASC and antibody secretion following the washing step and prior to measuring the number of ASC.

Similarly, disclosed herein are methods of diagnosing the presence of a disease or exposure to an antigen in a subject comprising obtaining whole blood, plasma, or PBMC from the subject between 3 and 45 days following antigenic exposure or during viral shedding, separating the plasma from the newly proliferated ASC, and measuring the number of ASC or antibodies from the isolated ASC specific for an antigen, wherein the presence of ASC or antibodies specific for the antigen indicates the subject as an ongoing infection with the source of the antigen. The disclosed methods of diagnosing or detecting exposure to an antigen can further comprise washing the newly proliferated ASC, wherein the washed ASC comprise at least a two, three, four, five, six, seven, eight, nine, ten, 15, 20, 25, 30, 40, 50, 60, 70, 80, 90, 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC and incubating the newly proliferated ASC in a media that supports maintenance of ASC and antibody secretion following the washing step and prior to measuring the number of ASC.

It is understood and herein contemplated that to avoid the results being confounded by pre-existing antibodies or circulating ASC, newly proliferated ASC should be separated in one aspect ASC isolated from the whole blood or plasma obtained from the subject. As noted herein, this separation can be achieved by ficoll gradient centrifuagation, elutriation and the like or by antibody means such as fluorescence acquired cell sorting, magnetic bead sorting, and magnetic columns. Once separated, ASC can be washed one, two, three, four, five, six, seven, eight, nine, ten, or more times to remove residual contaminating PBMC, plasma, whole blood, or pre-existing antibodies. It is contemplated herein that the washed ASC comprise at least a two, three, four, five, six, seven, eight, nine, ten, 15, 20, 25, 30, 40, 50, 60, 70, 80, 90, 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC. The newly proliferated ASC can then be cultured for 1, 2, 3, 4, 5, 6, 7, or 8 hours (i.e., from 1 to 2, 1 to 3, 1 to 4, 1 to 5, 1 to 6, 1 to 7, 1 to 8, 2 to 3, 2 to 4, 2 to 5, 2 to 6, 2 to 7, 2 to 8, 3 to 4, 3 to 5, 3 to 6, 3 to 7, 3 to 8, 4 to 5, 4 to 6, 4 to 7, 4 to 8, 5 to 6, 5 to 7, 5 to 8, 6 to 7, 6 to 8, or 7 to 8 hours) in a media conducive to production and expression of antibodies forming the analyte MENSA. The MENSA can comprise survival factors such as IL-2, IL-6, IL-15, IL-21, and IFN-α, APRIL, enhancers of antibody secretion such as IL-21, other non-antibody secreting cells such as T cells or macrophage, but not red blood cells. Also, depending on the ASC separation method employed, the MENSA may also contain magnetic beads or compounds needed for rapid separation of ASC from whole blood or plasma.

In one aspect, it is understood that detection can be accomplished by ELISA, chemiluminescence, ELIspot, surface plasmon resonance, and hospital modular alanyzers.

In another aspect disclosed herein are methods of assessing the efficacy of a vaccine in a subject comprising obtaining peripheral blood mononuclear cells (PBMC) from the subject between 3 and 45 days following administration of the vaccine, isolating MENSA, and measuring the number of antibody secreting cells (ASC) or antibodies in the MENSA, and comparing the number of ASC to a standard, wherein more ASC in the PBMC relative to a standard indicates an efficacious vaccine. Also disclosed are methods of assessing the effectiveness of a therapy for an autoimmune disease comprising obtaining ASC from the subject, isolating MENSA, and measuring the number of antibody secreting cells (ASC) or antibodies in the MENSA, wherein the absence of ASC indicates an effective therapy. It is understood and herein contemplated that because the methods of assessing the efficacy of a vaccine or a therapy for an autoimmune disease comprises obtaining MENSA, it is contemplated that the methods specifically contemplate the additional steps for obtaining MENSA into the disclosed assessing the level or detecting presence of antibody secreting cells methods. Thus, in one aspect, disclosed herein are methods of assessing the efficacy of a vaccine or a therapy for an autoimmune disease comprising obtaining whole blood, plasma, or PBMC from the subject between 3 and 45 days following antigenic exposure or during viral shedding; separating newly proliferated ASC from the plasma; washing the newly proliferated ASC, and measuring the number of ASC or antibodies from the isolated ASC specific for an antigen; and comparing the number of ASC to a standard or negative control; wherein the washed ASC comprise at least a two, three, four, five, six, seven, eight, nine, ten, 15, 20, 25, 30, 40, 50, 60, 70, 80, 90, 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC; wherein an increase of vaccine specific ASC or antibodies in the MENSA relative to a standard or control indicates an efficacious vaccine. It is further contemplated herein that the disclosed methods can further comprise incubating the newly proliferated ASC in a media that supports maintenance of ASC and antibody secretion following the washing step and prior to measuring the number of ASC.

"Efficacy," "efficacious," or "sufficiency" means the ability to function as intended. For example, an "efficacious" immune response is a response that is able to afford the subject an acceptable degree of immune protection from the immunizing antigen. Thus, the present methods disclose methods of assessing the ability of an immune response to provide immune protection against future antigenic encounter. Traditionally, such methods involve antigenic challenge. It is understood that the present methods provide an alternative means to achieve the goal of antigenic challenge and can be used separately or in conjunction with a challenge to determine efficacy or sufficiency.

Throughout this application the term "sufficient immune response" is used to describe an immune response of a large enough magnitude to provide an acceptable immune protection to the subject against future antigen encounter. It is understood that immune protection does not necessarily mean prevention of future antigenic encounter (e.g., infection), nor is it limited to a lack of any pathogenic symptoms. "Immune protection" means a prevention of the full onset of a pathogenic condition. Thus, in one embodiment, a "sufficient immune response" is a response that reduces the symptoms, magnitude, or duration of an infection or other disease condition when compared with an appropriate control. The control can be a subject that is exposed to an antigen before or without a sufficient immune response.

It is understood herein that an "immune response" refers to any inflammatory, humoral, or cell-mediated response that occurs for the purpose of eliminating an antigen. Such responses can include, but are not limited to, antibody production, cytokine secretion, complement activity, and cytolytic activity. In one embodiment, the immune response is an antibody response.

By "effective amount" is meant a therapeutic amount needed to achieve the desired result or results, e.g., establishing an immune response that can confer immunological protection to the subject. It is understood that immunological protection includes, but is not limited to, prevention of subsequent infections; reduction of the effects or symptoms of subsequent infections or conditions; reduction in the duration of the infection or condition; lessening of severity of a disease or condition; or reduced antigenic load relative to non-treated controls.

From an experimental standpoint, the assays and methods provided herein required optimization and adaptation of 3 steps of the current SOA Elispot: (1) separation of ASCs from plasma, (2) ASC secretion of newly expressed antibodies, and (3) detecting specificity of newly synthesized antibodies specific for influenza proteins.

Step 1: Typically the ASCs from the plasma, can be separated by ficoll density centrifugation. Although relatively easy in a research laboratory, this process is time and labor intensive and not amenable to hundreds of samples that would be needed in a clinical laboratory during an outbreak; therefore, rapid and easy ASC isolation is contemplated. Circulating ASCs maintain CD19 cell surface expression and high levels of CD38 expression. These are lead candidate markers that can be used to isolate ASC. The data show that negative or positive magnetic ASC isolation of CD19+ and/or CD38+ cells from magnetic beads preserves spontaneous antibody production from the blood.

Step 2: Once newly blasted ASCs are separated from the plasma, ASC are washed in accordance with the disclosure herein. Washed ASC comprise at least a two, three, four, five, six, seven, eight, nine, ten, 15, 20, 25, 30, 40, 50, 60, 70, 80, 90, 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC.

Step 3: Once newly blasted ASCs are separated from the plasma, ASC are cultured for antibody secretion or elaboration. Circulating ASCs removed directly ex vivo secrete enough pathogen-specific antibodies within 1 hour as measured by Elispots. Therefore, less than 1 hour is sufficient for the production of measureable antibodies. Shorter antibody elaboration times reduce antibody amounts. In another embodiment antibody secretion is enhanced from these cells with cytokines such as IL-2, IL-6, IL-15, IL-21, and IFN-α as well as other potential enhancers.

Step 4: The standard detection method by the ASC Elispot is highly sensitive with low background noise since it measures antibodies from a single cell. Unfortunately, Elispot assays can be time intensive and difficult to automate. Hence, measuring pathogen-specificity from total secreted antibodies from an entire population of isolated ASCs makes the process more streamlined. The data illustrate secretion rates from an individual circulating ASC at 10 pg per hour. However, higher secreted antibody concentrations can be achieved by increasing the blood sample volume (or more ASC) and/or by decreasing the elaboration volume or concentrating MENSA. The pathogen-specific antibodies are measured by conventional enzyme-linked methods which can detect in range of ng/mL and/or by chemiluminescence which has reliable detection limits of pg/mL ($10^{-12}$ M). Thus, these two methods were incorporated to validate MENSA fluid. There are two major advantages of MENSA. First, lower limits of microbe-specific antibodies in MENSA are well within the limits of detection of modular analyzers in most hospitals. The second major advantage of the MENSA fluid is the low background due to a single analyte (only the newly synthesize antibodies) captured in the media. This is unlike plasma that contains numerous proteins including all types of antibodies. Because of its cleanliness, the MENSA matrix is amenable to label-free detection methods and many ultra-sensitive detector methods due to the high signal to noise ratio. Thus, in one aspect detection can be accomplished by ELISA, chemiluminescence, ELIspot, surface plasmon resonance, and hospital modular alanyzers.

The need for knowing the sufficiency of an immune response is directly related to the need to administer one or more subsequent vaccines to a subject with an insufficient response. Referred to as a booster immunization, these subsequent vaccine administrations elevate immune response to protective levels. Accordingly, disclosed herein are methods of assessing the need of the administration of a booster immunization in a subject comprising obtaining peripheral blood mononuclear cells (PBMC), whole blood, or plasma from the subject between 3 and 45 days following administration of a vaccine, separating newly activated ASC from the PBMC, whole blood, or plasma; washing the ASC; culturing the ASC in media conducive to antibody production and expression (MENSA); and measuring the number of antibody secreting cells (ASC) or antibodies in the MENSA, and comparing the number of ASC or antibodies to a standard, wherein fewer ASC or antibodies in the MENSA relative to a standard indicates the need for an immunization boost.

Disclosed herein are methods of determining antigen exposure in a subject comprising obtaining peripheral blood mononuclear cells (PBMC) from the subject and measuring the presence of antibody secreting cells (ASC) in the PBMC, wherein the presence of ASC indicates antigen exposure. It is understood and herein contemplated that the existence of antigen-specific ASC is indicative of an infection. Accordingly, the present methods of determining antigen exposure in a subject can be used to diagnose a subject with an infectious, autoimmune, or parasitic disease wherein the presence of antigen-specific ASC indicates a subject has the disease from which the antigen was derived. In the case of an autoimmune disease the antigen would be from the subject. Accordingly, disclosed herein are methods of diagnosing a subject with a disease comprising obtaining peripheral blood mononuclear cells (PBMC) from the subject and measuring the presence of antibody secreting cells (ASC) in the PBMC, wherein the presence of ASC indicates the subject has the disease. In one aspect, the ASC being detected is MENSA. Thus, in one aspect, disclosed herein are methods of determining antigen exposure in a subject comprising obtaining MENSA from the subject and measuring the presence of MENSA, wherein the presence of MENSA indicates antigen exposure.

Similarly, due to the specificity conferred by the methods disclosed herein, it is possible to make differential diagnoses among various potential causative agents. By utilizing panels of antigens that are associated with similar types of diseases, a diagnosis of the particular cause of the symptoms of a subject may be determined. For example, the methods disclosed herein can be used to determine the whether a subject has including; Influenza Virus/viral subtype panel: which can distinguish causative organisms including but not limited to Influenza A, Influenza B, Influenza A: H1N1 swine, Influenza A: H1N1 New Caedonia/Brisbane/Solomon Islands; Influenza A: H3N2 Wisconsin/Wyoming/Brisbane, Influenza A: H5N1, Influenza A: H7, NP, and Influenza: H9. Alternatively, the methods disclosed herein can be used to determine if an upper respiratory infection is due to *S. pneumoniae, Pneumococcal Pheumonia, Pneumococcal Epyema, H. influenzae, Legionella, Mycoplasma, Moraxella, S. aureus, Klebsiella pneumoniae, Pseudomonas aeruginosa, E. coli, Chlamydophila pneumoniae*, RSV, Influenza A+B, Parainfluenza, Human metapneumovirus, Rhinovirus, Coronavirus, Adenovirus, SARS, TB, and Coccidiomycoses.

Similarly, the methods disclosed herein can be used to assess the immune response to an allergen. Current methods of determining allergic reactions include the "scratch test" and ELISAs. The scratch test is an assay where an abrasion is created on the subject's skin and a potential allergen applied directly to the abrasion. A qualitative assessment is then made to determine whether any observed inflammation is of a significant enough amount to be considered an allergic response. This assay is an uncomfortable process for the subject and prone to false positives as a strong response in one abrasion site can carry over to neighboring sites. By utilizing the ASC methods disclosed herein, a panel of allergens can be tested in vitro so less discomfort is created for the subject. Moreover, an exact quantification of the allergen specific ASC can be determined Thus, rather than a qualitative assay based on perceived inflammation, the exact amount of IgE baring ASC specific for the allergen can be quantified creating no chance of a false positive. Accordingly, disclosed herein are methods of diagnosing the presence of an allergy in a subject comprising obtaining peripheral blood mononuclear cells (PBMC) from the subject and measuring the presence of antibody secreting cells (ASC) in the PBMC, wherein the presence of ASC indicates antigen exposure.

The methods disclosed herein comprise assessing the efficacy or sufficiency of an immune response to a selected antigen in a subject as well as diagnosing a disease or identifying antigen exposure in a subject. The disclosed methods utilize tissue samples from the subject to provide the basis for assessment. Such tissue samples can include, but are not limited to, blood (including peripheral blood and peripheral blood mononuclear cells), tissue biopsy samples (e.g., spleen, liver, bone marrow, thymus, lung, kidney, brain, salivary glands, skin, lymph nodes, and intestinal tract), and specimens acquired by pulmonary lavage (e.g., bronchoalveolar lavage (BAL)). Thus, it is understood that the tissue sample can be from both lymphoid and non-lymphoid tissue. Examples of non-lymphoid tissue include but are not limited to lung, liver, kidney, and gut. Lymphoid tissue includes both primary and secondary lymphoid organs such as the spleen, bone marrow, thymus, and lymph nodes. In one aspect the analyte under examination is MENSA.

In one aspect, the methods disclosed herein make diagnoses, measure exposure, or determine efficacy, effectiveness, or need for further treatment through the measure of the number of presence of antibody secreting cells (ASC) or antibodies. It is understood and herein contemplated that "antibody secreting cell" or "plasma cell" refers to any B lineage cell capable of secreting antibody including but not limited to plasmablasts, short-lived antibody secreting cells, long-lived plasma cell. It is further understood and specifically contemplated that the presence or number of such cells can be determined by any of the immunoassays disclosed herein, including but not limited to ELISPOT assay. It is further understood that where a ELISPOT assay is used to measure the presence or level of antibody secreting cells to a particular antigen, that ELISPOT assay can be antigen specific.

It is understood and herein contemplated that the disclosed methods can be performed with MENSA, ASC, or antibodies obtained 3, 4, 5, 6, 7, 8, 9, 10, 11, 12, 13, 14, 15, 20, 25, 30, 35, 40, or 45 days following antigenic exposure (including but not limited to infection and vaccination). In one aspect the PBMC are obtained between 3 and 45 days following antigenic exposure. In another aspect, the PBMC are obtained between 3 and 30 days following antigenic exposure. In another aspect, the PBMC are obtained between 3 and 20 days following antigenic exposure. In another aspect, the PBMC are obtained between 3 and 15 days following antigenic exposure. In another aspect, the PBMC are obtained between 3 and 12 days following antigenic exposure. In another aspect, the PBMC are obtained between 3 and 10 days following antigenic exposure. In another aspect, the PBMC are obtained between 5 and 10 days following antigenic exposure. In yet another aspect, the PBMC are obtained between 5 and 8 days following antigenic exposure. Therefore, disclosed herein are methods of assessing the need of the administration of a booster immunization in a subject comprising obtaining antigen specific antibody secreting cells (ASC), antibodies, or MENSA from the subject between 3 and 45 days following antigenic exposure, such as, for example, administration of a vaccine or infection and measuring the number of antigen specific antibody secreting cells (ASC), antibodies, or MENSA, wherein detection of antigen specific antibodies, ASC, or MENSA indicates a recent exposure to the antigen. It is understood and herein contemplated that because the methods of assessing the need of the administration of a booster immunization comprises obtaining MENSA, it is contemplated that the methods specifically contemplate the additional steps for obtaining MENSA into the disclosed assessing the need of the administration of a booster immunization methods. Thus, in one aspect, disclosed herein are methods of assessing the need of the administration of a booster immunization comprising obtaining whole blood, plasma, or PBMC from the subject between 3 and 45 days following antigenic exposure or during viral shedding; separating the newly proliferated ASC from the plasma; washing the newly proliferated ASC, wherein the washed ASC comprise at least a two, three, four, five, six, seven, eight, nine, ten, 15, 20, 25, 30, 40, 50, 60, 70, 80, 90, 100, 150, 200, 250, 300, 400, 500, 600, 700, 800, 900, $10^3$, $2\times10^3$, $3\times10^3$, $4\times10^3$, $5\times10^3$, $6\times10^3$, $7\times10^3$, $8\times10^3$, $9\times10^3$, $10^4$, $10^5$, $10^6$, $10^7$-fold reduction of contaminating pre-existing plasma antibodies relative to whole blood, plasma, or PBMC; and measuring the number of antigen specific antibody secreting cells (ASC), antibodies, or MENSA, wherein detection of antigen specific antibodies, ASC, or MENSA indicates a recent exposure to the antigen. It is further contemplated herein that the disclosed methods can further comprise incubating the newly proliferated ASC in a media that supports maintenance of ASC and antibody secretion following the washing step and prior to measuring the number of ASC.

In a further aspect, the disclosed methods can be modified to determine the efficacy of a vaccination and thus enable the physician to make a determination whether additional vaccinations are needed to form a protective immune response. Where, efficacy of a vaccination is being determined, the methods further comprise comparing the number of ASC or antibodies to a standard, wherein fewer ASC or antibodies in the PBMC or MENSA relative to a standard indicates the need for an immunization boost.

The kits and methods disclosed herein (including the diagnostic and exposure detection methods) are based on the ability of the methods to detect and distinguish antigenic exposure. "Antigen" means any native or foreign substance that is capable of eliciting an immune response. Preferably, the antigen will elicit an antibody, plasma cell, plasmablast, or B-cell response. Such antigens can include but are not limited to peptides and/or proteins from a subject, virus, bacteria, yeast, or parasite, including but not limited to toxins. Antigens can also include vaccines (e.g., peptides, proteins, killed pathogens, or attenuated pathogens administered in a pharmaceutically acceptable carrier either prophylactically or therapeutically), bio-warfare agents, and native peptides, polypeptides, and proteins.

It is understood that the antigen of any of the diagnostic methods and kits or antigenic exposure methods and kits can be a viral antigen. Viral antigens can include any peptide, polypeptide, or protein from a virus. Thus in one embodiment the antigen can be an antigen from a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A (including H1N1 or other Swine H1), Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

In particular, it is understood that the viral antigen can be an antigen from Influenza-A. Therefore it is understood that the present methods include methods of assessing the efficacy or sufficiency of an immune response to an Influenza-A antigen. Preferably the Influenza-A antigen is an attenuated or killed strain of Influenza-A.

Also disclosed are diagnostic methods and kits or antigenic exposure methods and kits wherein the antigen is a bacterial antigen. The antigen, for example, can be a peptide, polypeptide, or protein selected from the group of bacteria consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pneumoniae, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani, Clostridium difficile*, other *Clostridium* species, *Yersinia enterolitica*, and other *Yersinia* species.

Also disclosed are diagnostic methods and kits or antigenic exposure methods and kits wherein the antigen is a fungal antigen. The antigen can be, for example, a peptide, polypeptide, or protein selected from the group of fungi consisting of *Candida albicans, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi*, and *Alternaria alternata*.

Also disclosed are diagnostic methods and kits or antigenic exposure methods and kits wherein the antigen is a parasite antigen. The antigen can be, for example, a peptide, polypeptide, or protein selected from the group of parasitic organisms consisting of *Toxoplasma gondii, Plasmodium falciparum, Plasmodium vivax, Plasmodium malariae*, other *Plasmodium* species, *Trypanosoma brucei, Trypanosoma cruzi, Leishmania major*, other *Leishmania* species, *Schistosoma mansoni*, other *Schistosoma* species, and *Entamoeba histolytica*.

Also disclosed are diagnostic methods and kits or antigenic exposure methods and kits wherein the antigen is a toxin. It is understood that such toxins can include but are not limited to Abrin, Conotoxins Diacetoxyscirpenol Bovine spongiform encephalopathy agent, Ricin, Saxitoxin, Tetrodotoxin, epsilon toxin, *Botulinum* neurotoxins, Shigatoxin, *Staphylococcal* enterotoxins, T-2 toxin, Diphtheria toxin, Tetanus toxoid, and pertussis toxin.

Also disclosed are diagnostic methods and kits or antigenic exposure methods and kits wherein the antigen is a cancer-related antigen. The antigen can be, for example, a peptide, polypeptide, or protein selected from the group of cancers consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Thus, it is contemplated herein that, in one aspect, the disclosed methods can be used to distinguish/diagnose infection with a particular causative agent resulting in, for example, a respiratory infection. It is further understood that due to the specificity of the disclosed methods and MENSA, the methods can be used to make more specific distinctions such as the causative agent in community acquired pneumonia, the type and viral subtype of influenza infection, diagnose the species of *Mycobacterial* infection; determine the cause of pediatric upper respiratory infection, determine the causative agent of ventilator associated pneumonia, determine the causative agent involved in cystic fribrosis, determine the infection in a immunocompromised host, distinguish allergy from non-allergic responses, detect bioterroism agent, distinguish the causative agents of a hepatitis, determine the caustic agent in pediatric or traveler's diarrhea, determine the causative agent in diarrhea not associated with travel, determine the causative agent for abdomen-pertonittis/abscess, determine the causative agent in sexually transmitted diseases, determine the causative agent for a urinary tract infection, determine the causative agent for septiv arthritis, determine the causative agent for endocartitis, determine the causative agent for catherter related infections, determine the causative agent for osteomyelitis, determine the causative agent for cellulitis, determine the causative agent for diabetic foot infection, determine the causative agent in pediatric fevers, meningitis, encephalitis, and distinguish fungus pathogen vs. colonization.

Thus, in one aspect, panels can be prepared to make these above noted differential diagnoses. For example, disclosed herein are methods of diagnosing a patient comprising panels of interest include but are not limited to Respiratory panels: to diagnose the microbial etiology of pneumonia, COPD exacerbation; Upper Respiratory Infections: which can distinguish causative organisms including but not limited to one or more of *S. pneumoniae, H. influenzae, Legionella, Mycoplasma, Moraxella, S. aureus, Klebsiella pneumoniae, Pseudomonas aeruginosa, E. coli, Chlamydophila pneumoniae*, RSV, Influenza A+B, Parainfluenza, Human metapneumovirus, Rhinovirus, Coronavirus, Adenovirus, SARS, TB, and Coccidiomycoses; Influenza Virus/viral subtype panel: which can distinguish causative organisms including but not limited to one or more of Influenza A, Influenza B, Influenza A: H1N1 swine, Influenza A: H1N1 New Caedonia/Brisbane/Solom on Islands; Influenza A: H3N2 Wisconsin/Wyoming/Brisbane, Influenza A: H5N1, Influenza A: H7, NP, and Influenza: H9; Mycobacterial panel: which can distinguish *Mycobacterium tuberculosis, Mycobacterium avium, Mycobacterium bovis, Mycobacterium kansasii, Mycobacterium cheloni*, and *Mycobacterium gordonnae*; Pediatric Otitis/respiratory panel: which can distinguish causative organisms including but not limited to one or more of Strep pneumonia, *H. influenza, Legionella, Mycoplasma, Staph aureus, Moraxella*, RSV, Influenza A+B, Parainfluenza, Human metapneumovirus, Rhinovirus, Coronavirus, Adenovirus, Group A Strep, and Epstein Barr Virus (Acute Mononucleosis); Ventilator Associated Pneumonia panel: which can distinguish *S. aureus, P. aeruginosa; Stentotrophomonas, Acenitobacter, Enterobacteriacie, E. coli, K. Pneumoniae*, and Herpes Simplex Virus; a Cystic Fibrosis Panel: which can distinguish *P. aeruginosa, S. Aureus, Stenotrophomonas, Acinetobacter, Enterobacteracie, E. Coli*, and *K. Pneumoniae*; An allergy panel which can distinguish IgE from IgG; a Immunocompromised Host Panel which can distinguish *S. Pneumoniae, H. Influenzae, L. pneumonia, Mycoplasma, Morexella, S. aureus, K. pneumonia, P. aeruginosa, E. coli, Chlamydiophila pneumoniae*, Respiratory Syncytial Virus, Influeinza Virus A or B, Parainfluenza virus, Human Metapneumovirus, Rhimovirus, Coronavirus, Adenovirus, Group A Strep, and Acute Mononucleosis; Endocarditis Panel: which can distinguish causative organisms including but not limited to one or more of *Staph Aureus, Staph Epidermidis*, Beta hemolytic and alpha hemolytic Streptococci, Enterococcal and non-enteroccocal Group D *streptococcus, Candida*, and HACEK (*Hemophilus, Actinobacillus, Cariobacterium, Eikenella*, and *Kingella*) organisms; Sexually Transmitted Disease (Pelvic Inflammatory Disease) Panel: which can distinguish causative organisms including but not limited to one or more of Syphillis, Gonorrhea, Chlamydia, Herpes Simplex I+II; Meningitis/Encephalitis Panel: which can distinguish causative organisms including but not limited to one or more of *Strep pneumoniae, Listeria, H. influenza, Staph Aureus*, HSV, West Nile, Eastern Equine, Western Equine, LaCross, Jamestown canyon, St Louis, and Lymphocytic choriomeningitis virus; Septic Arthritis Panel: which can distinguish causative organisms including but not limited to one or more of Gonorhhea, *Staph Aureus, streptococcus*, and Coagulase negative staph; Osteomyelitis Panel: which can distinguish causative organisms including but not limited to one or more of *Staph aureus, Pseudomonas, Stenotrophomonas, Serratia, acinetobacter, enterobacter* sp., *E. Coli, Klebsiella* sp., Coagulase negative staph, *corynebacterium, Bacteroides fragilis*, beta hemolytic *streptococcus*, alpha hemolytic *streptococcus*, and *Enterococcus* sp.; Soft Tissue/Cellulitis Panel: which can distinguish causative organisms including but not limited to one or more of *Staph aureus, Pseudomonas, Serratia, acinetobacter, enterobacter* sp., *E. Coli, Klebsiella* sp., beta hemolytic *streptococcus*; Diabetic Foot Infection Panel: which can distinguish causative organisms including but not limited to one or more of *Staph aureus, Pseudomonas, Stenotrophomonas, Serratia, acinetobacter, enterobacter* sp., *E. Coli, Klebsiella* sp., Coagulase negative staph, *corynebacterium, Bacteroides fragilis*, beta hemolytic

*streptococcus*, alpha hemolytic *streptococcus*, and *Enterococcus* sp.; Fungal pathogen vs. colonization Panel: which can distinguish causative organisms including but not limited to one or more of *Aspergillus, candida, histoplasmosis, mucormycosis*, and *blastomycosis coccioides immitis*; Distinguish acute *mycobacterium* TB with chronic mTB; distinguish a line infection panel vs. colonization: which can distinguish causative organisms including but not limited to one or more of *Staph Aureus, S. Epidermis*, Coagulase negative staph, and *corynebacterium*; diagnosis of *staphylococcus* true line infection from blood culture contaminant; distinguish the patients with true blood borne infections compared to colonization, for example, through autolysin detection; diagnose acute Mononucleosis, or CMV panel; Hepatitis Panel: which can distinguish causative organisms including but not limited to one or more of Hepatitis A, B, C and delta, Herpes Simplex virus, Human Cytomegalovirus, and Epstein Barr Virus; GI Abscess Panel: which can distinguish causative organisms including but not limited to one or more of Gram negative (*E. Coli, Pseudomonas, B. Fragilis, Enterococcus, Staph Aureus*; Ventilator Associated Pneumonia VAP/(Hospital Acquired Pneumonia) HAP—a diagnostic panel which can distinguish causative organisms including but not limited to one or more of *Staph Aureus, Pseudomonas, Stenotrophomonas, acinetobacter, enterobacter* sp., *E. Coli, Kebsiella* sp., and serratia HSV; Urinary Tract Panel: which can distinguish causative organisms including but not limited to one or more of *E. Coli, Pseudomonas, enterococcus*, group B strep, *Klebsiella, Staph saprophyticus, Enterobacter* sp, and *Proteus* sp.; Pediatric Diarrhea Panel: which can distinguish causative organisms including but not limited to one or more of Rotovirus and Enterovirus; Traveler's Diarrhea Panel: which can distinguish causative organisms including but not limited to one or more of *Giardia, Salmonella*; Parasitic infection, *Shigella, Campylobacter, E. coli* 0157:H7, *Cyclospora*, and *Cryptosporidium*, General Diarrhea Panel: which can distinguish causative organisms including but not limited to one or more of *Giardia, Salmonella*; Parasitic infection, *Shigella, Campylobacter, E. coli* 0157:H7, *Cyclospora, C. Difficile*, and *Cryptosporidium*, Pediatric Fever Panel: HHV6, HSV, RSV, Influenza, Strep Pneumonia, and Group A strep.; and Bioterriorism panel: which can detect exposure to Anthrax, H5N1, SARS, and Smallpox.

The present methods can also be used to test the efficacy of immune responses to an antigen related to an autoimmune or inflammatory condition. Such conditions include but are not limited to asthma, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, myocardial infarction, Alzheimer's disease, transplant rejection (allogeneic and xenogeneic), thermal trauma, any immune complex-induced inflammation, glomerulonephritis, myasthenia gravis, cerebral lupus, Guillaine-Barre syndrome, vasculitis, systemic sclerosis, anaphylaxis, catheter reactions, atheroma, infertility, thyroiditis, ARDS, post-bypass syndrome, hemodialysis, juvenile rheumatoid, Behcets syndrome, hemolytic anemia, pemphigus, bulbous pemphigoid, stroke, atherosclerosis, and scleroderma. In particular, the antigen can comprise an amyloid antigen (e.g., amyloid β peptide) thus providing an assessment of an immune response to Alzheimer's disease. Thus, disclosed herein are methods of assessing the effectiveness of a therapy for an autoimmune disease comprising obtaining peripheral blood mononuclear cells (PBMC) from the subject and measuring the presence of antibody secreting cells (ASC) in the PBMC, wherein the absence of ASC indicates an effective therapy.

Application for the clinical use of the ASC Elispots directly ex vivo from the human blood include: diagnosis of acute microbial infections such as viral, fungal, bacterial infections (especially difficult to diagnosis invasive *Staphyloccoal* infections especially MRSA vs. colonization, bacterial pneumonia: *pneumococcal*, etc. fungal infections in the lung, CNS, or other invasive sites (i.e. *histoplasmosis, coccidiomycoses, cryptococcus*, etc.)); diagnosis of invasive vs. colonization of common flora such as *Candida* and *staphylococcus*; diagnosis of microbial exposure leading to autoimmune diseases; early biomarkers of antibody responses especially to assess humoral vaccine responses; identifying transplant recipients who may be at risk of developing alloantibodies post-tranplantation; and/or clinical assessment of general state of inflammation due to B cells by the increase in background frequencies of total Ig ASC (marker of inflammation such as CRP etc.).

Immunoassays

As shown herein, ASC can be detected by ELISPOT, but the transient presence of the antigen-specific ASC could also be used by detection of antigen-specific antibody secreted by the cells by ELISA which may be easier for clinical diagnostic laboratories to perform. ASC may also be detected by an immuno array or similar protein array or microarray The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy 492/515; Bodipy493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Di1 (Di1C18(3)); I Dinitrophenol; DiO (DiOC18(3)); DiR; DiR (Di1C18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane;

MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl)quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection.

Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody—antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods.

Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromogenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated *staphylococcal* Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum/plasma. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunospot Assay (ELISPOT is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, *staphylococcal* nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. In this assay a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, *staphylococcal* nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with aminoor aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in E. coli, after selection from phage or ribosome display libraries (Cambridge Antibody Technology, Cambridge, UK; Biolnvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into $E.\ coli$, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

1. Antibodies

As used herein, the term "antibody" encompasses, but is not limited to, whole immunoglobulin (i.e., an intact antibody) of any class. Native antibodies are usually heterotrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain antigen binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522-525 (1986); Riechmann et al., *Nature,* 332:323-327 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.,* 151:2296 (1993) and Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Disclosed are hybidoma cells that produces the monoclonal antibody. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA,* 81:6851-6855 (1984)).

Monoclonal antibodies may be prepared using hybridoma methods, such as those described by Kohler and Milstein, *Nature,* 256:495 (1975) or Harlow and Lane. *Antibodies, A Laboratory Manual.* Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of an antigen expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. *Hybridoma.* 1998 December; 17(6):569-76; Kilpatrick K E et al. High-affinity monoclonal antibodies to PED/PEA-15 generated using 5 microg of DNA. *Hybridoma.* 2000 August; 19(4):297-302, which are incorporated herein by referenced in full for the the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of antigen-specific antibody as fusion proteins. The antigen is produced by inserting a gene fragment in-frame between the signal sequence and the mature protein domain of the antigen-specific antibody nucleotide sequence. This results in the display of the foreign proteins on the surface of the virion. This method allows immunization with whole virus, eliminating the need for purification of target antigens.

Generally, either peripheral blood lymphocytes ("PBLs") also referred to as peripheral blood mononuclear cells (PBMC) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103) Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.*, 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against an antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane *Antibodies, A Laboratory Manul* Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816, 567) or by covalently joining to the immunoglobulin coding sequence all or part of the coding sequence for a non-immunoglobulin polypeptide.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, *Antibodies, A Laboratory Manual*, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) *Synthetic Peptides: A User Guide*. W.H. Freeman and Co., N.Y. (1992); Bodansky M and Trost B., Ed. (1993) *Principles of Peptide Synthesis*. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science*, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) *FEBS Lett*. 307:97-101; Clark-Lewis I et al., *J. Biol. Chem.*, 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. *Nucl. Acids Res.* 10:6487-500 (1982).

A variety of immunoassay formats may be used to select antibodies that selectively bind with a particular protein, variant, or fragment. For example, ELISPOT and solid-phase ELISA immunoassays are routinely used to select antibodies selectively immunoreactive with a protein, protein variant, or fragment thereof. See Harlow and Lane. *Antibodies, A Laboratory Manual*. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., *Anal. Biochem.*, 107:220 (1980).

Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits can include magnetic beads or antibodies for use in separating newly proliferated ASC from plasma such as anti-CD38, anti-CD19, or anti-Cd27 antibodies or magnetic beads as well as the necessary labware to perform the isolation. Kits can also include media and enhancers to stimulate antibody production in MENSA. The kits can include antigens to coat the wells of microtiter plates for diagnosis, efficacy, or biodetection assays embodied in some of the methods, as well as the primary antibody, and reagents required to detect the antibody as intended. It is further understood that the kit can further comprise secondary antibodies and assay support structures such as, for example, microtiter plates. For example, disclosed are kits for diagnosing the presence of a disease or exposure to an antigen in a subject comprising one or more antigens, a first antibody, and one or more reagents for detecting the presence of the first antibody. Also disclosed are kits for assessing a subject's need for further vaccination comprising an antigen, a primary antibody, a secondary antibody, a detectable agent and a microtiter plate. Also disclosed herein are kits for diagnosing the presence of a disease or condition in a subject. Further disclosed herein are kits for making a differential diagnosis among various causative agents that could be the cause of a disease or condition (e.g., determining the pathogenic cause of an upper respiratory infection or distinguishing amongst strains of influenza).

In one aspect, the disclosed kits can further comprise instructions directing the practitioner to wash the newly proliferated and separated ASC sufficiently to obtain at least a two, three, four, five, six, seven, eight, nine, ten, 15, 20, 25, 30, 40, 50, 60, 70, 80, 90, 100, 150, 200, 250, 300, 400, 500, 600, 700, 800, 900, $10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $10^4$, $10^5$, $10^6$, $10^7$-fold reduction of contaminating pre-existing plasma antibodies relative to whole blood, plasma, or PBMC. Additionally, the disclosed kits can comprise a washing solution as disclosed herein to perform the washing.

Also provided is an antibody reagent kit comprising containers of the monoclonal antibody or fragment thereof and one or more reagents for detecting binding of the antibody or fragment thereof to an antigen. The reagents can include, for example, fluorescent tags, enzymatic tags, or other tags. The reagents can also include secondary or tertiary antibodies or reagents for enzymatic reactions, wherein the enzymatic reactions produce a product that can be visualized. The reagents can further include a microtiter plate with nitrocellulose wells.

It is further understood that wherein a kit may detect the presence of exposure to an antigen or diagnose the presence of disease, the kits disclosed herein can comprise one or more antigens creating a panel to target assessments. For example, the kit can be provided to assess one or more respiratory ailments, one or more diseases that can cause endocartits, one or more diseases that can cause septic arthritis, fungi, or distinguish among hepatitis strains.

It is understood and herein contemplated that the kits disclosed herein can comprise any array of panels to which antigens exist. Such panels are extremely useful where the necessity to determine the causative agent of a condition will effect the treatment, such as, for example, making a diagnosis between viral strains or between a causative agent which may be bacterial, viral, fungal, or parasitic. Additionally, such panels can be useful in distinguishing between the presence of a line infection or blood borne infection from colonization. For example, a hospital could determine whether an entering patient had a staph infection prior to admission rather than acquired while an occupant of a hospitals facilities. Thus, also disclosed herein are methods of diagnosing a subject with a disease or exposure to an antigen (for example, an infection present in a subject prior to being admitted to a health care facility) comprising obtaining peripheral blood mononuclear cells (PBMC) from the subject and measuring the presence of antibody secreting cells (ASC) in the PBMC, wherein the presence of ASC indicates an a subject has been exposed to an antigen. Such methods can include one or more antigens on a single assay plate or assay system (including flow cytometry) such that a panel of antigens is created.

Panels of interest include but are not limited to Respiratory panels: to diagnose the microbial etiology of pneumonia, COPD exacerbation; Upper Respiratory Infections: which can distinguish causative organisms including but not limited to one or more of *S. pneumoniae, H. influenzae, Legionella, Mycoplasma, Moraxella, S. aureus, Klebsiella pneumoniae, Pseudomonas aeruginosa, E. coli, Chlamydophila pneumoniae*, RSV, Influenza A+B, Parainfluenza, Human metapneumovirus, Rhinovirus, Coronavirus, Adenovirus, SARS, TB, and Coccidiomycoses; Influenza Virus/viral subtype panel: which can distinguish causative organisms including but not limited to one or more of Influenza A, Influenza B, Influenza A: H1N1 swine, Influenza A: H1N1 New Caedonia/Brisbane/Solom on Islands; Influenza A: H3N2 Wisconsin/Wyoming/Brisbane, Influenza A: H5N1, Influenza A: H7, NP, and Influenza: H9; Mycobacterial panel: which can distinguish *Mycobacterium tuberculosis, Mycobacterium avium, Mycobacterium bovis, Mycobacterium kansasii, Mycobacterium cheloni*, and *Mycobacterium gordonnae*; Pediatric Otitis/respiratory panel: which can distinguish causative organisms including but not limited to one or more of *Strep pneumonia, H. influenza, Legionella, Mycoplasma, Staph aureus*, Moraxella, RSV, Influenza A+B, Parainfluenza, Human metapneumovirus, Rhinovirus, Coronavirus, Adenovirus, Group A Strep, and Epstein Barr Virus (Acute Mononucleosis); Ventilator Associated Pneumonia panel: which can distinguish *S. aureus, P. aeruginosa; Stentotrophomonas, Acenitobacter, Enterobacteriacie, E. coli, K. Pneumoniae*, and Herpes Simplex Virus; a Cystic Fibrosis Panel: which can distinguish *P. aeruginosa, S. Aureus, Stenotrophomonas, Acinetobacter, Enterobacteracie, E. Coli*, and *K. Pneumoniae*; An allergy panel which can distinguish IgE from IgG; a Immunocompromised Host Panel which can distinguish *S. Pneumoniae, H. Influenzae, L. pneumonia, Mycoplasma, Morexella, S. aureus, K. pneumonia, P. aeruginosa, E. coli, Chlamydiophila pneumoniae*, Respiratory Syncytial Virus, Influeinza Virus A or B, Parainfluenza virus, Human Metapneumovirus, Rhimovirus, Coronavirus, Adenovirus, Group A Strep, and Acute Mononucleosis; Endocarditis Panel: which can distinguish causative organisms including but not limited to one or more of *Staph Aureus, Staph Epidermidis, Beta hemolytic* and alpha hemolytic Streptococci, Enterococcal and non-enteroccocal Group D *streptococcus, Candida*, and HACEK (*Hemophilus, Actinobacillus, Cariobacterium, Eikenella*, and *Kingella*) organisms; Sexually Transmitted Disease (Pelvic Inflammatory Disease) Panel: which can distinguish causative organisms including but not limited to one or more of Syphillis, Gonorrhea, Chlamydia, Herpes Simplex I+II; Meningitis/Encephalitis Panel: which can distinguish causative organisms including but not limited to one or more of *Strep pneumoniae, Listeria, H. influenza, Staph Aureus*, HSV, West Nile, Eastern Equine, Western Equine, LaCross, Jamestown canyon, St Louis, and Lymphocytic choriomeningitis virus; Septic Arthritis Panel: which can distinguish causative organisms including but not limited to one or more of Gonorhhea, *Staph Aureus, streptococcus*, and Coagulase negative staph; Osteomyelitis Panel: which can distinguish causative organisms including but not limited to one or more of *Staph aureus, Pseudomonas, Stenotrophomonas, Serratia, acinetobacter, enterobacter* sp., *E. Coli, Klebsiella* sp., Coagulase negative staph, *corynebacterium, Bacteroides fragilis*, beta hemolytic *streptococcus*, alpha hemolytic *streptococcus*, and *Enterococcus* sp.; Soft Tissue/Cellulitis Panel: which can distinguish causative organisms including but not limited to one or more of *Staph aureus, Pseudomonas, Serratia, acinetobacter, enterobacter* sp., *E. Coli, Klebsiella* sp., beta hemolytic *streptococcus*; Diabetic Foot Infection Panel: which can distinguish causative organisms including but not limited to one or more of *Staph aureus, Pseudomonas, Stenotrophomonas, Serratia, acinetobacter, enterobacter* sp., *E. Coli, Klebsiella* sp., Coagulase negative staph, *corynebacterium, Bacteroides fragilis*, beta hemolytic *streptococcus*, alpha hemolytic *streptococcus*, and *Enterococcus* sp.; Fungal pathogen vs. colonization Panel: which can distinguish causative organisms including but not limited to one or more of *Aspergillus, candida, histoplasmosis, mucormycosis*, and *blastomycosis* coccioides immitis; Distinguish acute *mycobacterium* TB with chronic mTB; distinguish a line infection panel vs. colonization: which can distinguish causative organisms including but not limited to one or more of *Staph Aureus, S. Epidermis*, Coagulase negative staph, and *corynebacterium*; diagnosis of *staphylococcus* true line infection from blood culture contaminant; distinguish the patients with true blood borne infections compared to colonization, for example, through autolysin detection; diagnose acute Mononucleosis, or CMV panel; Hepatitis Panel: which can distinguish causative organisms including but not limited to one or more of Hepatitis A, B, C and delta, Herpes Simplex virus, Human Cytomegalovirus, and Epstein Barr Virus; GI Abscess Panel: which can distinguish causative organisms including but not limited to one or more of Gram negative (*E. Coli, Pseudomonas, B. Fragilis, Enterococcus, Staph Aureus*; Ventilator Associated Pneumonia VAP/(Hospital Acquired Pneumonia) HAP—a diagnostic panel which can distinguish causative organisms including but not limited to one or more of *Staph Aureus, Pseudomonas, Stenotrophomonas, acinetobacter, enterobacter* sp., *E. Coli, Kebsiella* sp., and serratia HSV; Urinary Tract Panel: which can distinguish causative organisms including but not limited to one or more of *E. Coli, Pseudomonas, enterococcus*, group B strep, *Klebsiella, Staph saprophyticus, Enterobacter* sp, and *Proteus* sp.; Pediatric Diarrhea Panel: which can distinguish causative organisms including but not limited to one or more of Rotovirus and Enterovirus; Traveler's Diarrhea Panel: which can distinguish causative organisms including but not limited to one or more of *Giardia, Salmonella*; Parasitic infection, *Shigella, Campylobacter, E. coli* 0157:H7, *Cyclospora*, and *Cryptosporidium*, General Diarrhea Panel: which can distinguish causative organisms including but not limited to one or more of *Giardia, Salmonella*; Parasitic infection, *Shigella, Campylobacter, E. coli* 0157:H7, *Cyclospora, C. Difficile*, and *Cryptosporidium*, Pediatric Fever Panel: HHV6, HSV, RSV, Influenza, Strep Pneumonia, and Group A strep.; and Bioterriorism panel: which can detect exposure to Anthrax, H5N1, SARS, and Smallpox.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Many vaccines induce immunological memory and establish long-term humoral protection against an infectious agent. The influenza vaccine has had mixed results depending on the similarity of the vaccine versus circulating strains. A good vaccine response induces long-term protection; however, identifying long-term responders is difficult without the tincture of time. Early biomarkers of long-term protective responses are needed especially in highly vulnerable populations such as the elderly, pregnant and immunocompromised patients.

Increase in neutralizing antibody titers is the conventional humoral immune markers of influenza vaccine responses. Antibody secreting cells (ASC) are responsible for the rise in antibody levels. Plasmablasts or ASCs are increased in the blood of human subjects after trivalent inactivated influenza (TIV) vaccination.

Trivalent influenza vaccination results in a transient burst of antigen-specific ASC in the peripheral blood, peaking at 5 to 9 days after vaccination and immediately disappearing. These cells are thought to be responsible for the 28 day rise in vaccine-specific antibody titers. While most of these plasmablasts undergo apoptosis, some migrate to the bone-marrow to become long-lived plasma cells. Identifying long-lived ASC or long-lived plasma cells subsets during this peripheral ASC burst functions as early biomarkers of long-term protective responses.

Figure 2A:
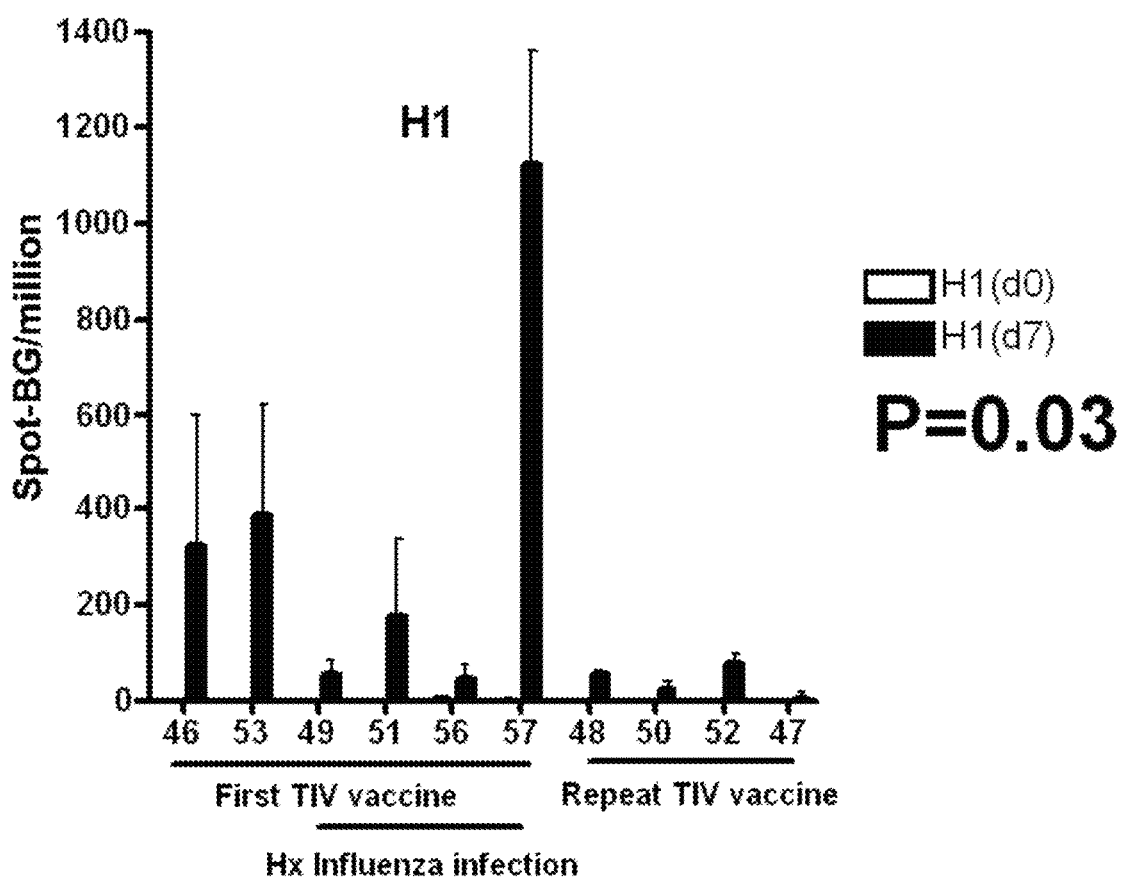
Figure 2B:
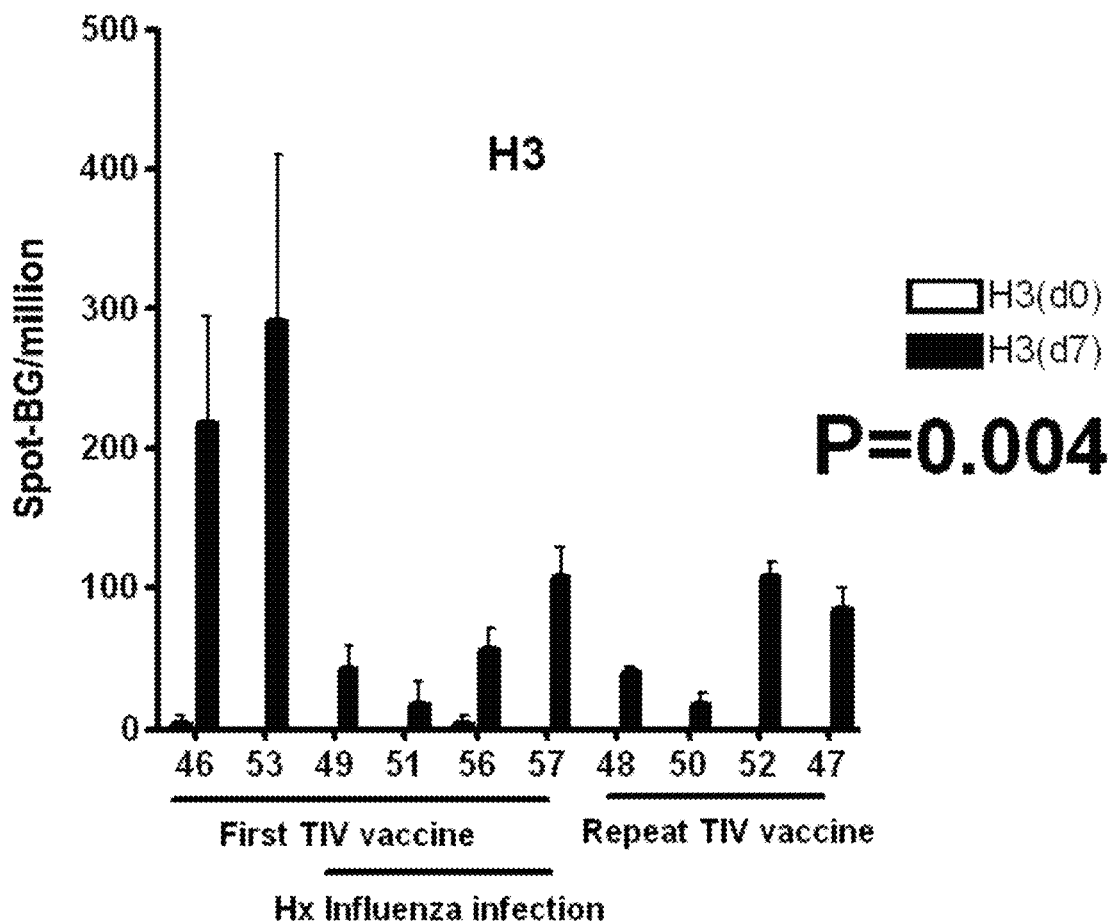
Figure 2C:
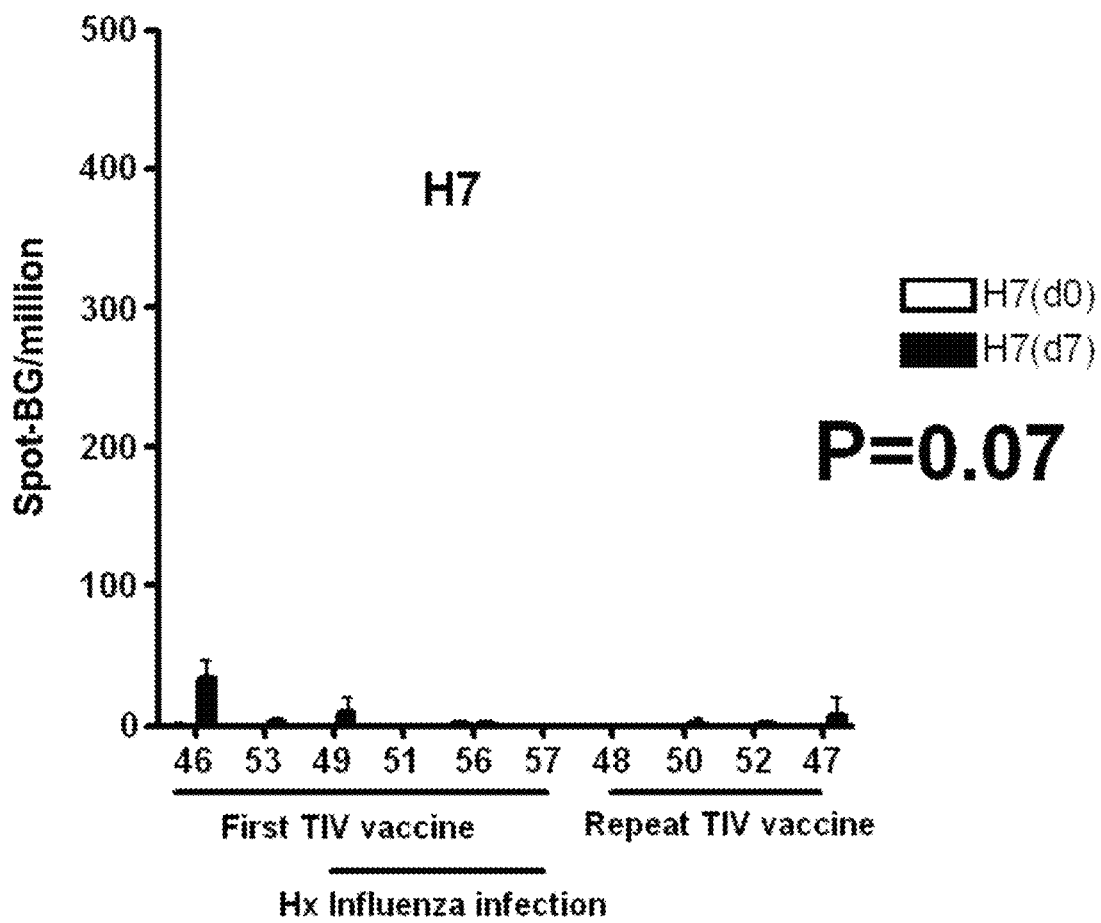
Figure 2D:
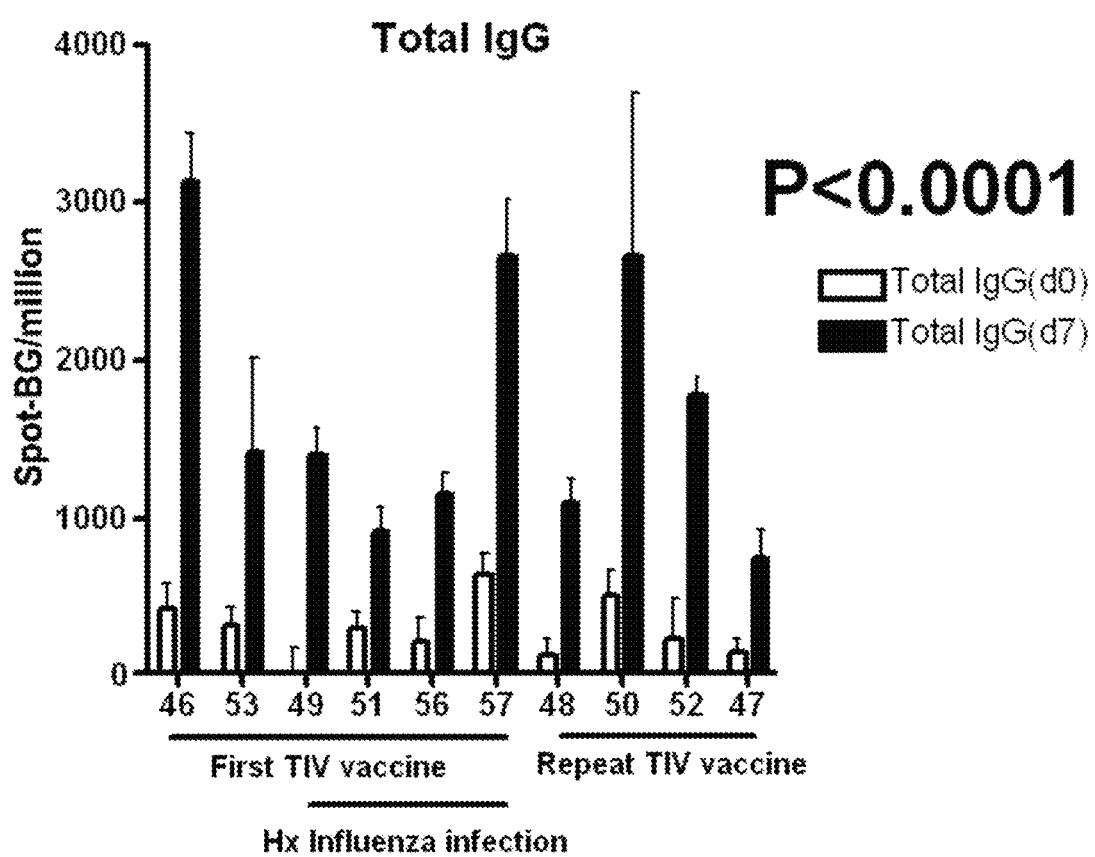
Figure 3A:
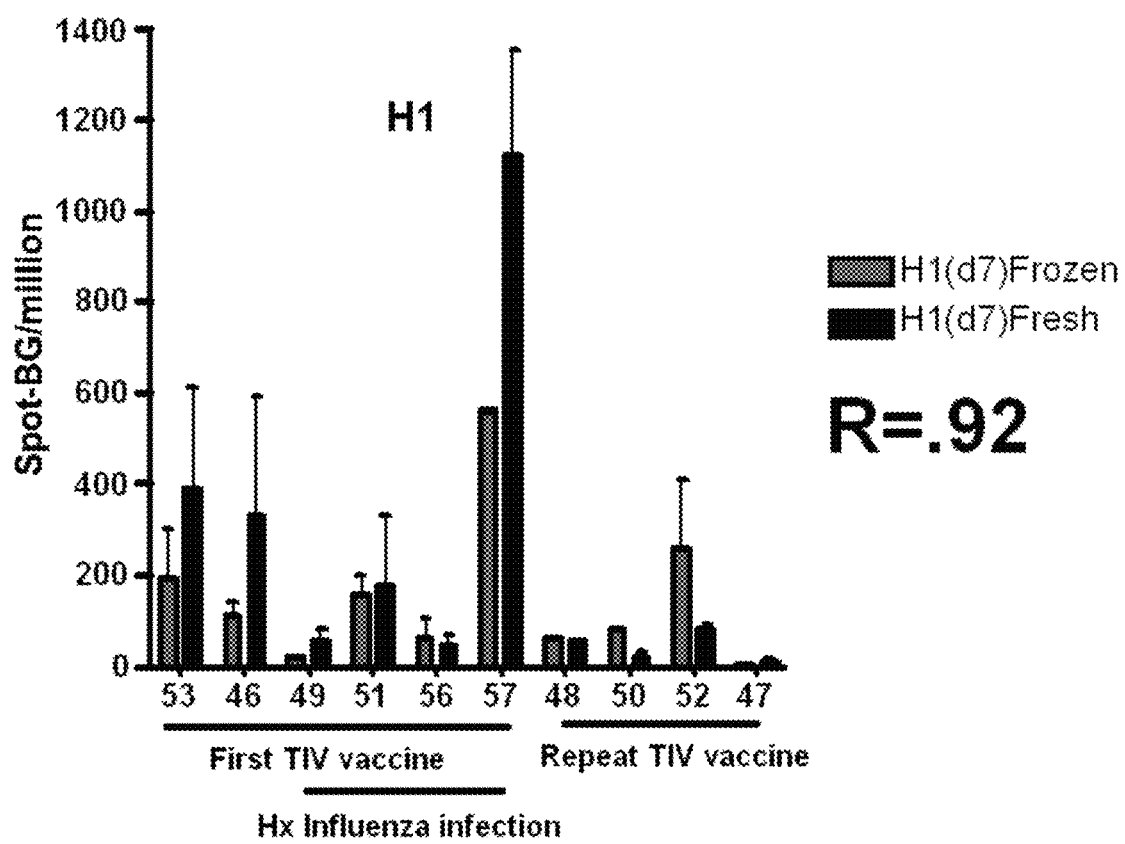
Figure 3B:
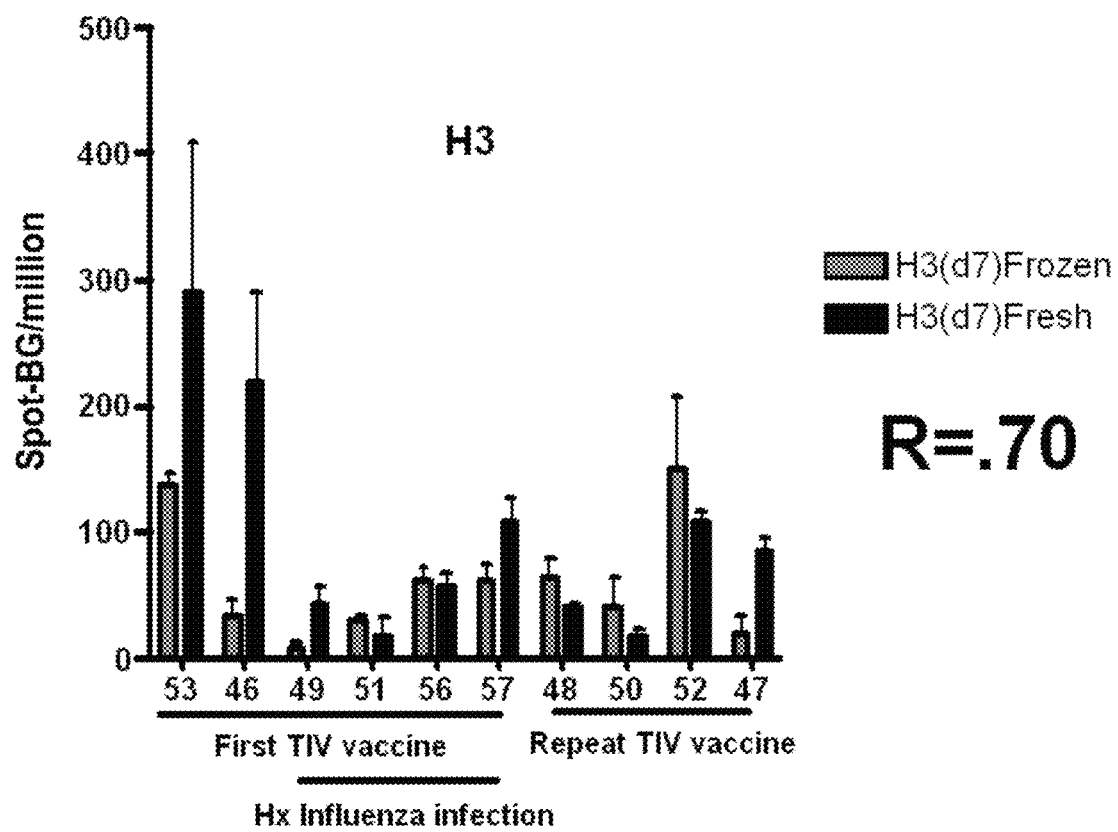
Figure 3C:
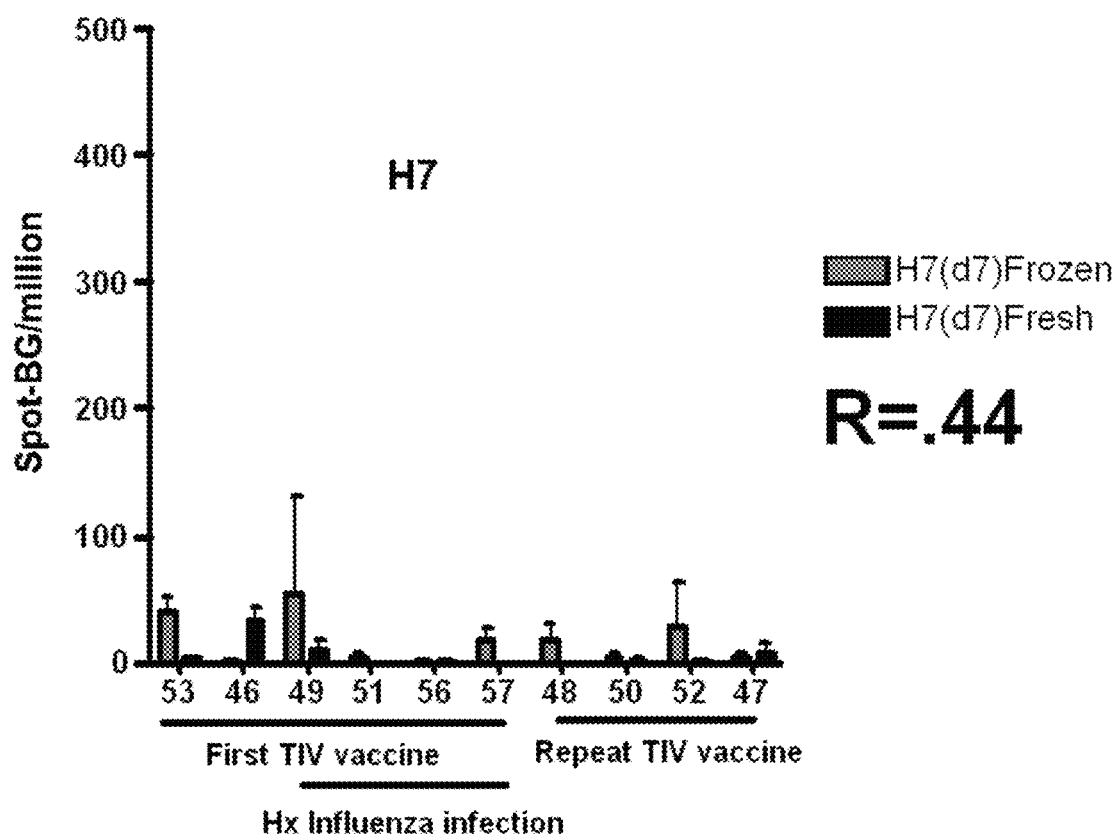
Figure 3D:
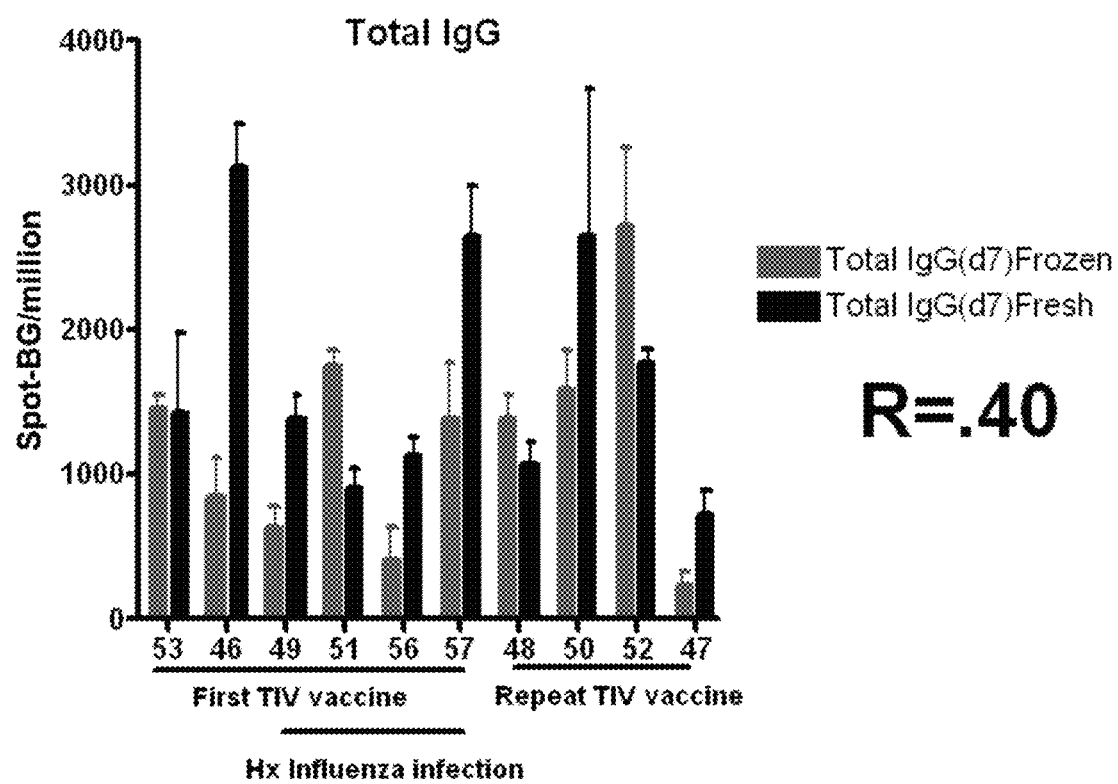

Demonstrated herein is that the influenza-specific H1 and H3 ASC Elispots can be detected 7 days post vaccination directly ex vivo from fresh and frozen peripheral blood (FIG. 1).

a) Results:

The frequency of influenza-specific ASC showed a significant increase 7 days after TIV in the peripheral blood. H1-, H3-, and H7-specific IgG ASC spots/million PBMC on day 7 were 229±341, 98±90, and 6±11 respectively (FIGS. 2A, 2B, and 2C). The percentage H1-, H3-, and H7-specific of total IgG ASC spots were 11.9±13.7, 6.3±5.8, and 0.3±0.5 respectively. Total IgG ASC spots/million PBMC pre- & 7-day post-vaccination were 290±188 (0.029% PBMC) and 1691±836 (0.17% PBMC) respectively (FIG. 2D). In contrast, no H1- and H3-specific IgG ASC were detected in any of the subjects on day 0 and 28. H7 antigens were used as negative controls.

Figure 4A:
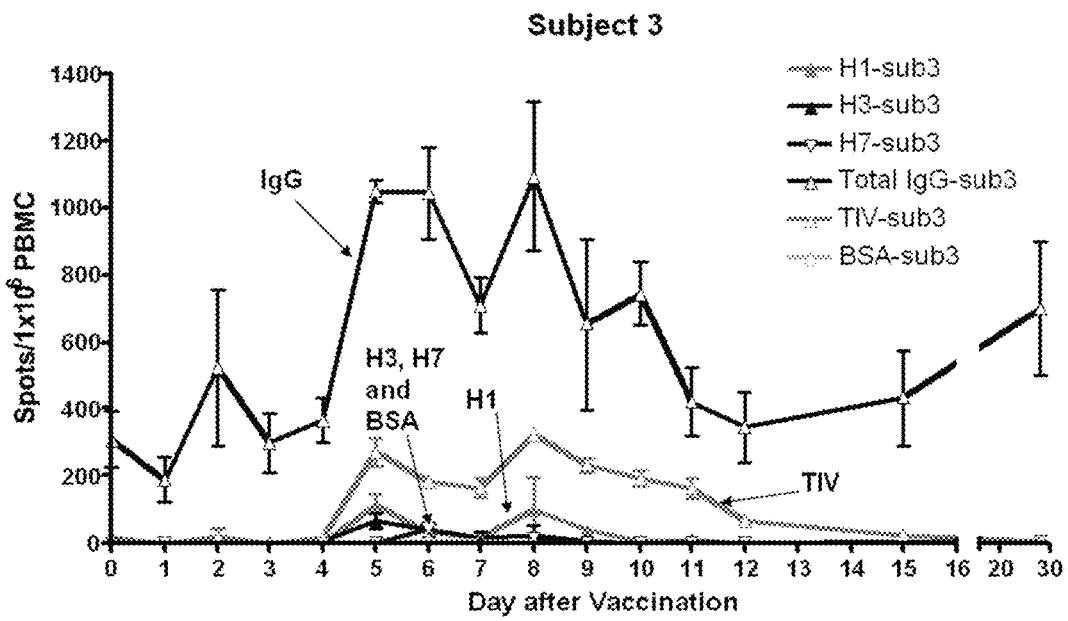
Figure 4B:
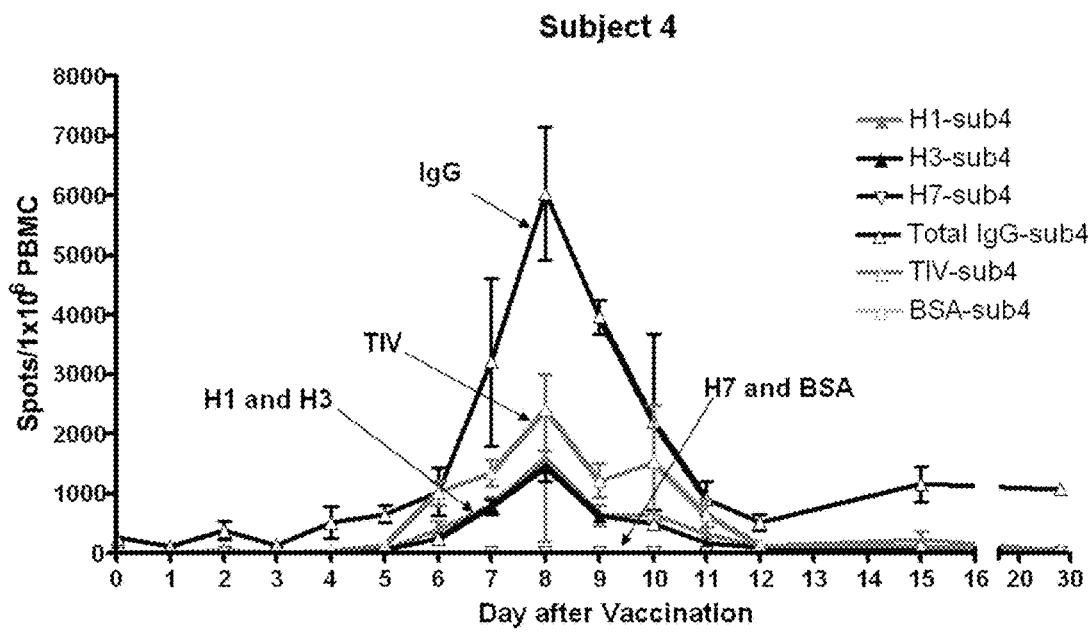

H1-H3-, H7- and total specific ASC IgG ELISpot frequencies in the fresh vs frozen PBMC on day 7 were similar (r=0.92, 0.70, 0.4 respectively) (FIGS. 3A, 3B, 3C, and 3D). Frequencies of total plasmablasts by flow cytometry (0.21±0.19% of PBMC) were similar to total IgG ASC spot frequencies suggesting most plasmablasts secreted IgG. Kinetics of influenza-specific ASC ex vivo peak on day 8 in subjects with no prior history of TIV (primary or naïve B cell response) (FIG. 4B). Rise in influenza-specific ASC have double peaks on day 5 and 8 post TIV in subjects with history of TIV (FIG. 4A). The double peak may suggest an of influenza-specific ASC from memory and naïve B cells respectively. TIV-specific ASC expansion is significantly higher in one subjects with no prior history of influenza vaccination or infection. A significant rise of TIV-specific and non-TIV-specific ASC ex vivo is shown demonstrating a potential non-TIV specific or bystander ASC responses.

TIV-specific ASC may be a useful early biomarker of vaccine responses.

b) Methods:

(1) Peripheral Blood Mononuclear Cells (PBMC) Separation

PBMC were isolated by ficoll separation and some cells were frozen. Assay were performed fresh or frozen.

(2) Antibody Secreting Cell (ASC) ELISpots 187. 96 well plates were coated with purified Influenza Hemagglutinin A from H1N1 (New Caledonia), H3N2 (Wisconscin) and H7N2 strains (Protein Science, Meriden, Conn.). Fresh or once frozen PBMCs taken at day 0, 7, or 28 from 10 young healthy subjects following TIV vaccination were incubated for 18 to 20 hours at 37° C. Cells were removed and alkaline-phosphatse conjugated goat-anti-human IgG (Jackson Immunoresearch) was incubated for 2 hours. Wells were developed and spots were counted using a CTL reader (Cellular Technologies Ltd).

(3) 11-Color FACS Analysis

Cell analysis was performed from fresh and frozen PBMC. (CD19, CD20, CD10, CD3, CD27, IgD, IgG, CD38). Samples were analyzed by Flowjo.

(4) Fresh vs. Frozen Study

Young healthy human subjects, between the ages of 19 to 32 years (mean±SD: 26±4), without concurrent illnesses were recruited at the University of Rochester Medical Center during 2006-2007. All subjects had not received the 2006-07 trivalent influenza vaccine (TIV). Blood was collected pre, 7 & 28 days post TIV. The history of influenza vaccinations and infections were collected from each subject.

(5) Daily Kinetics Study 190. 2 young healthy human subjects with the same criteria (see above) were recruited at the University of Rochester Medical Center during 2006-07. Blood was collected from these subjects pre, 1 through 12, 15 and 28 days after vaccination.

2. Example 2

There is no antigen-specific ASC in the blood of healthy human subjects without evidence of antigenic exposure. 16 healthy subjects were tested and none had H1, H3 or flu vaccine ASC in the blood. They all had some baseline total IgG ASC in the blood with a frequency of 296±148 per million PBMC.

Figure 5:
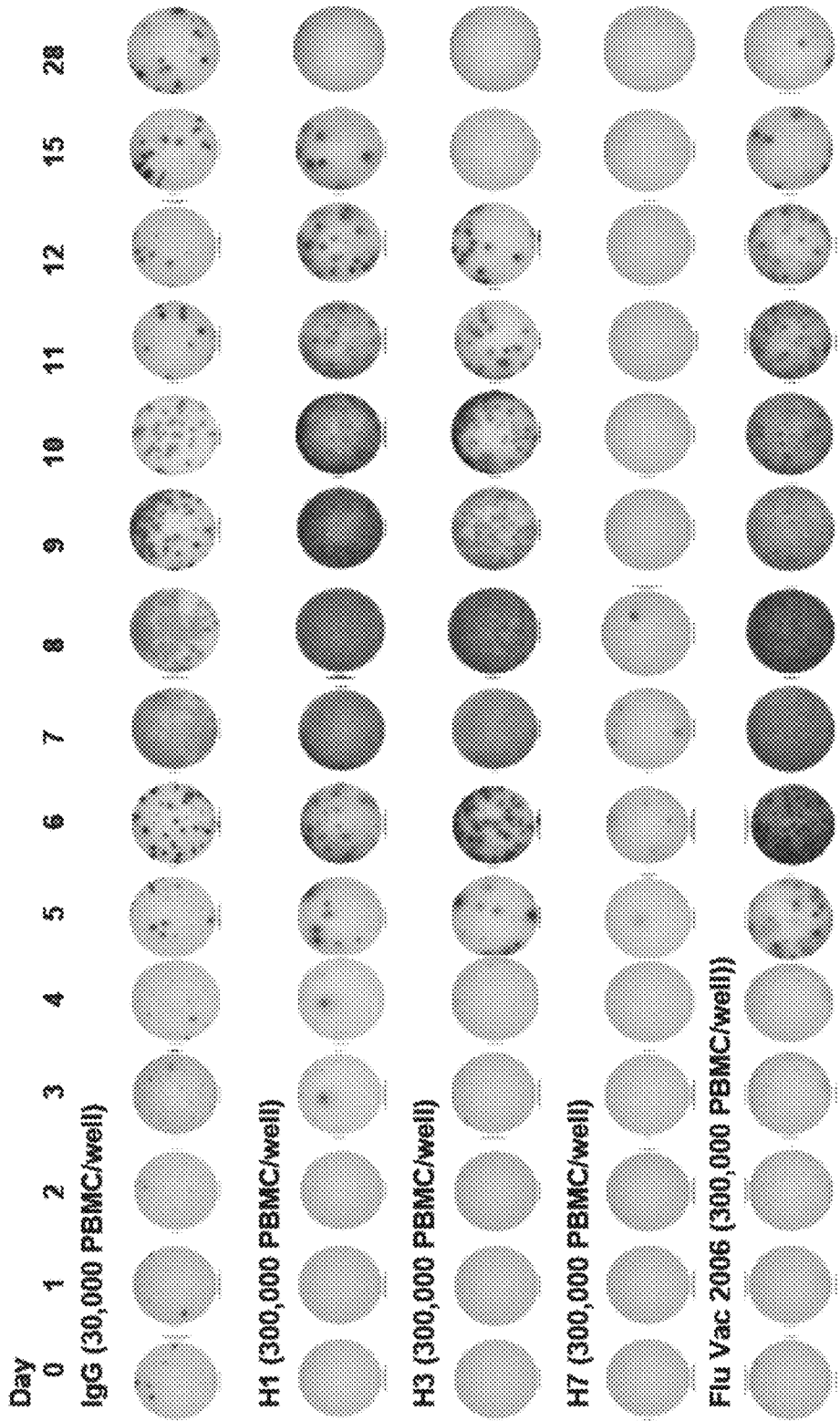
Figure 6A:
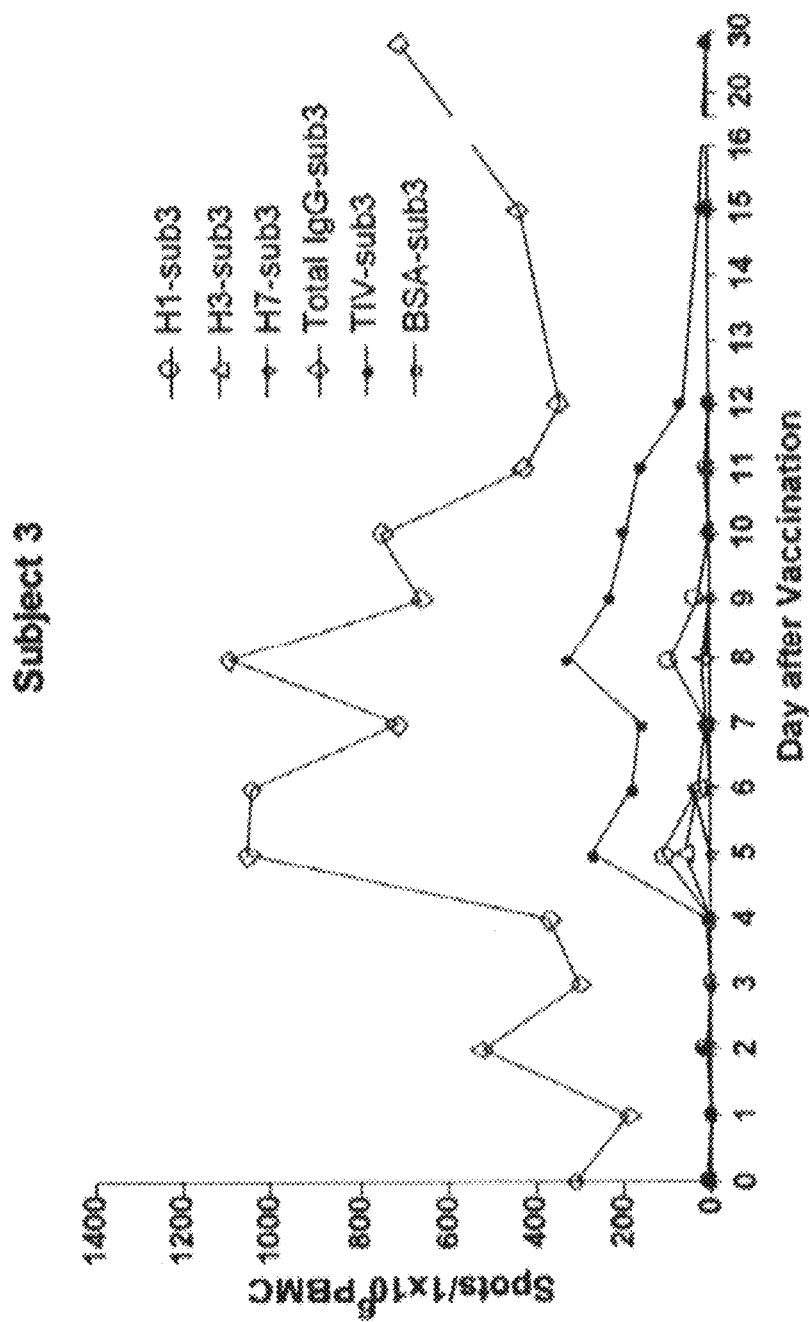
Figure 6B:
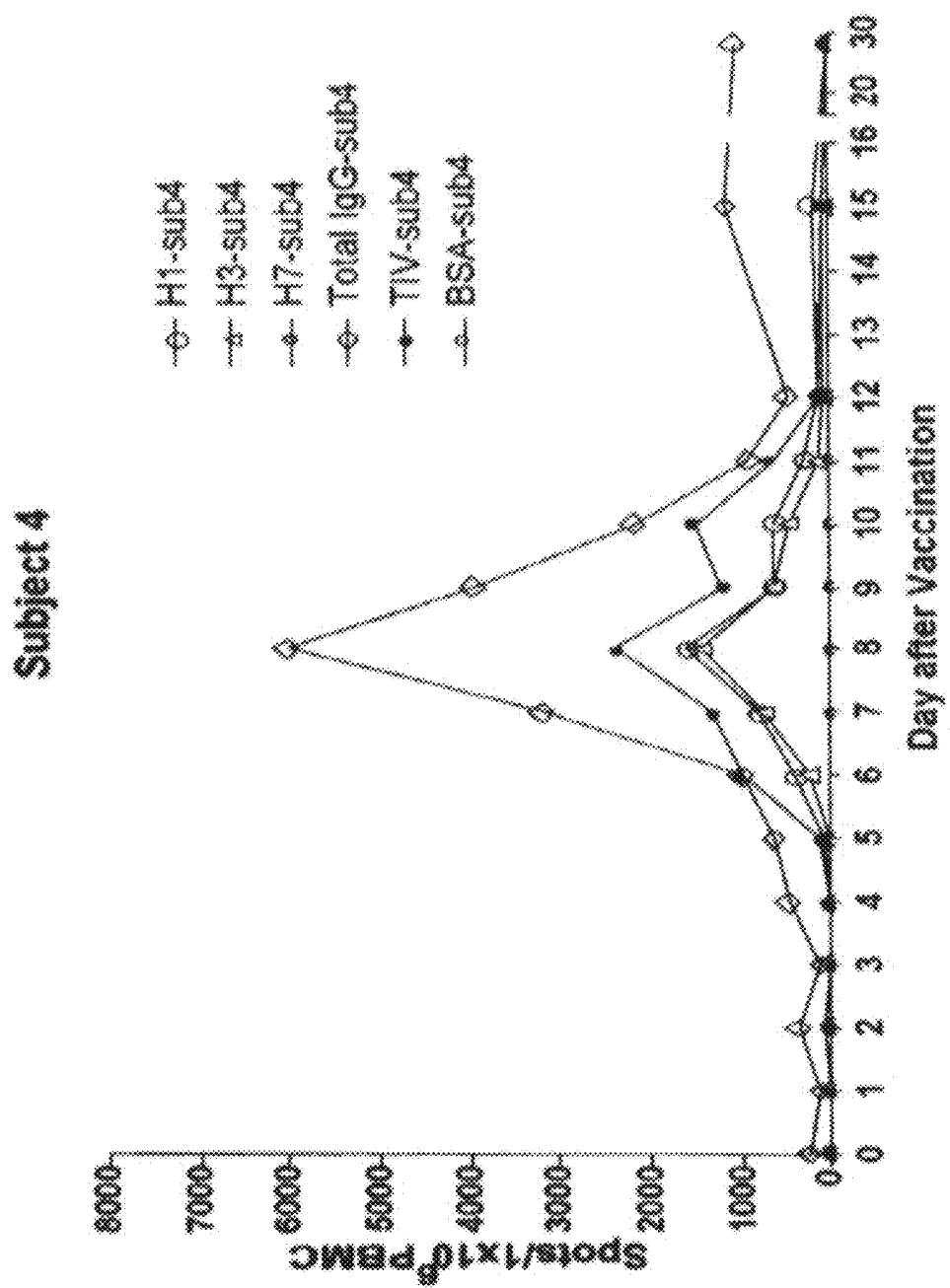
Figure 6C:
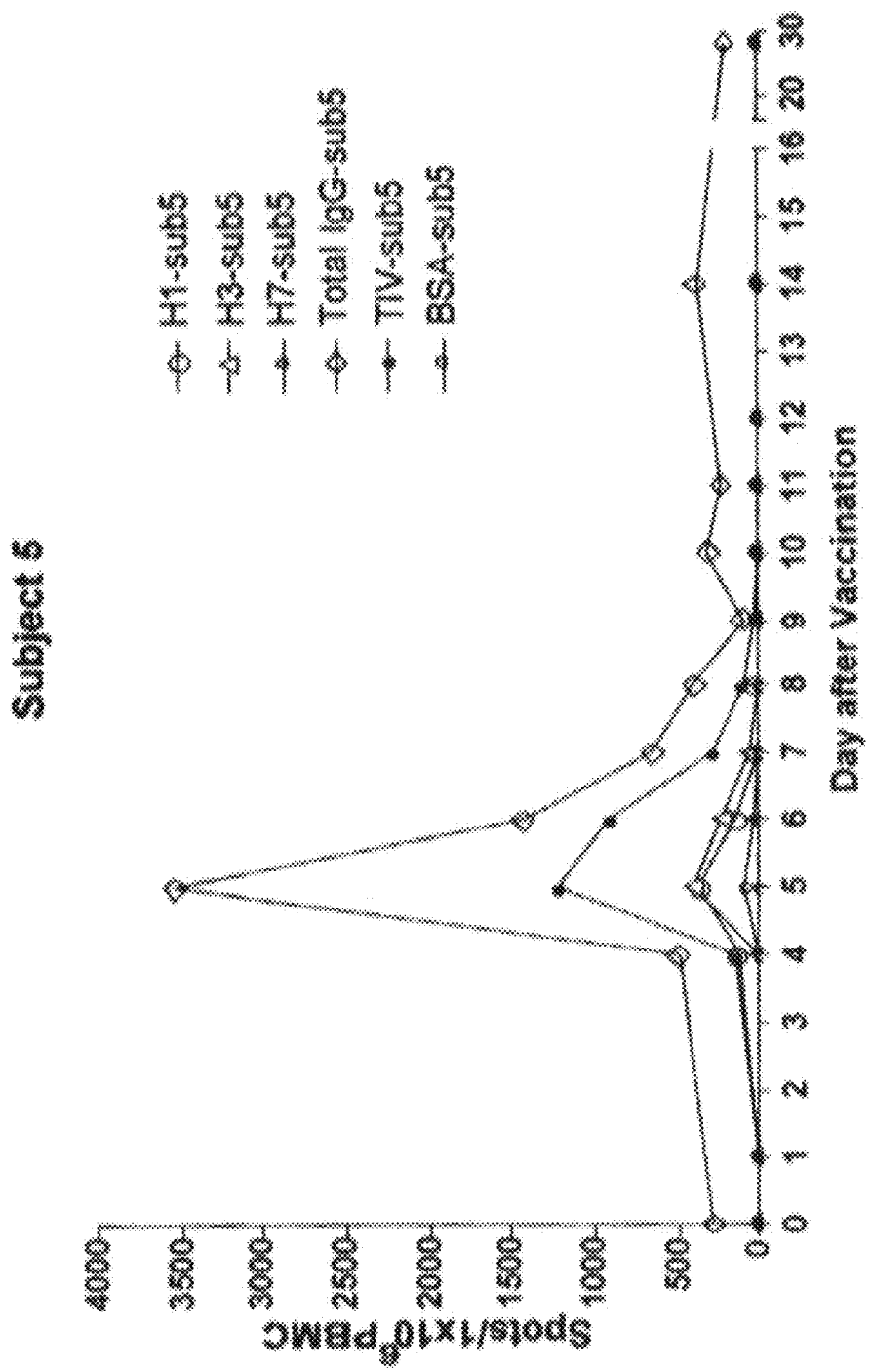
Figure 6D:
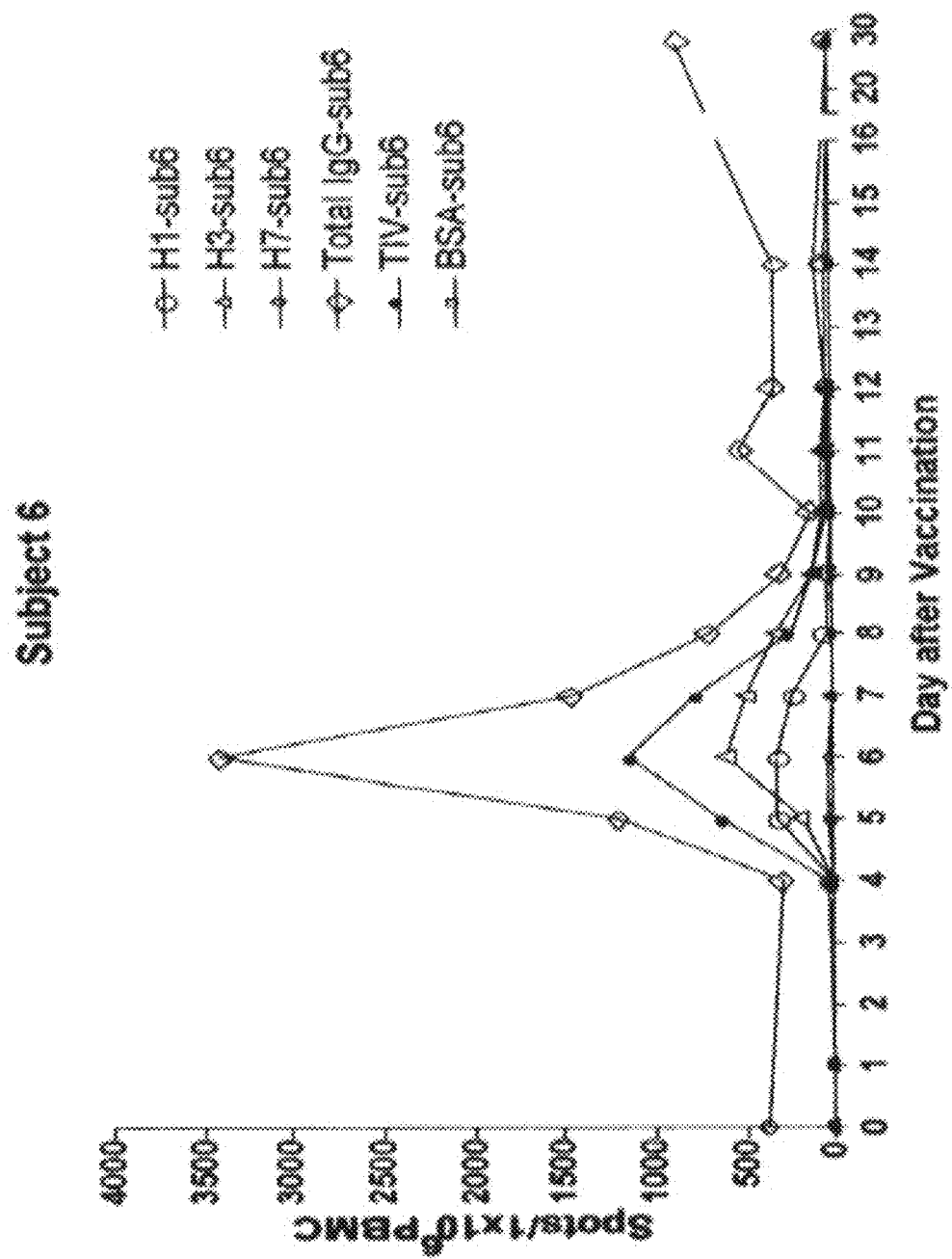
Figure 6E:
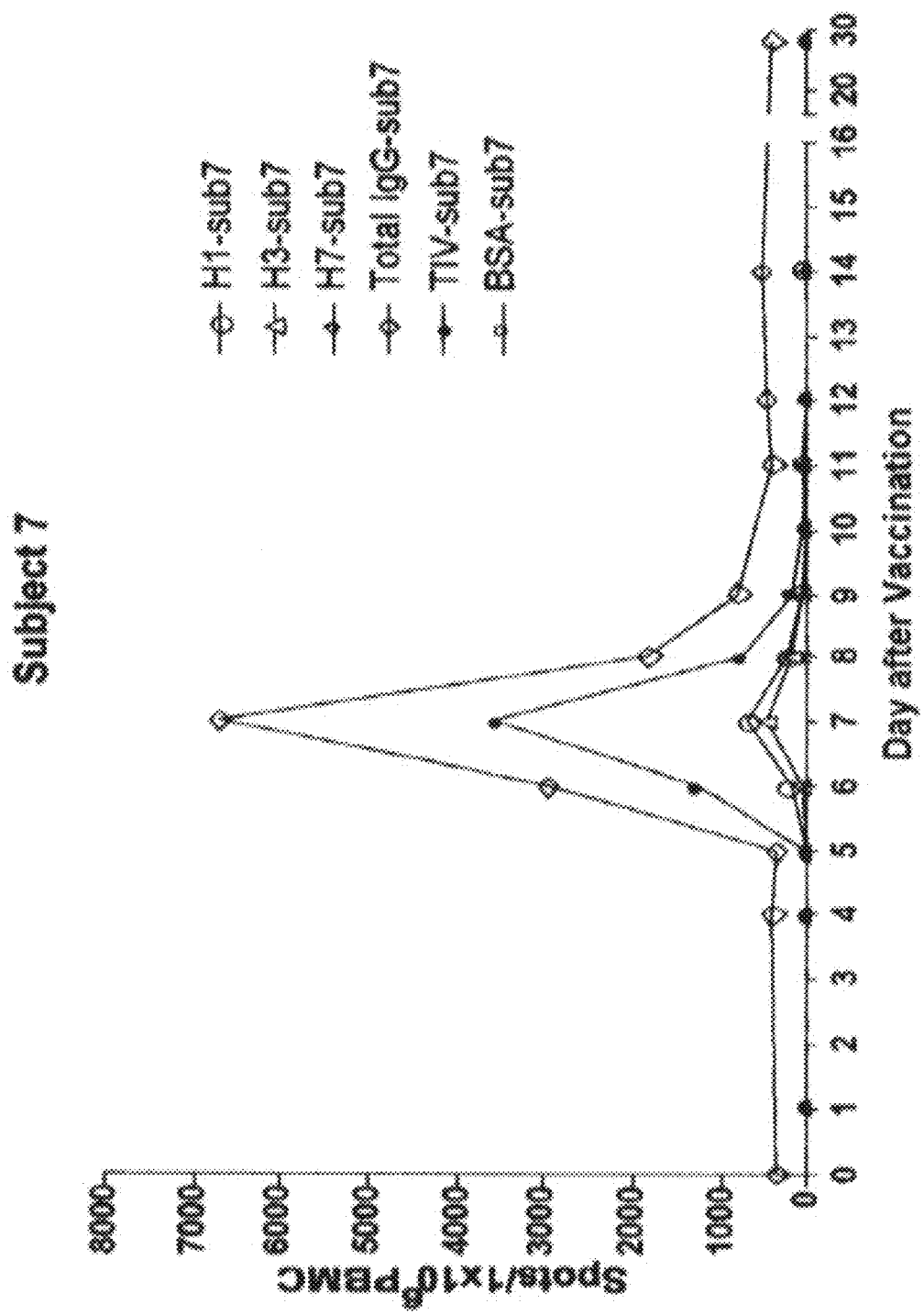
Figure 6F:
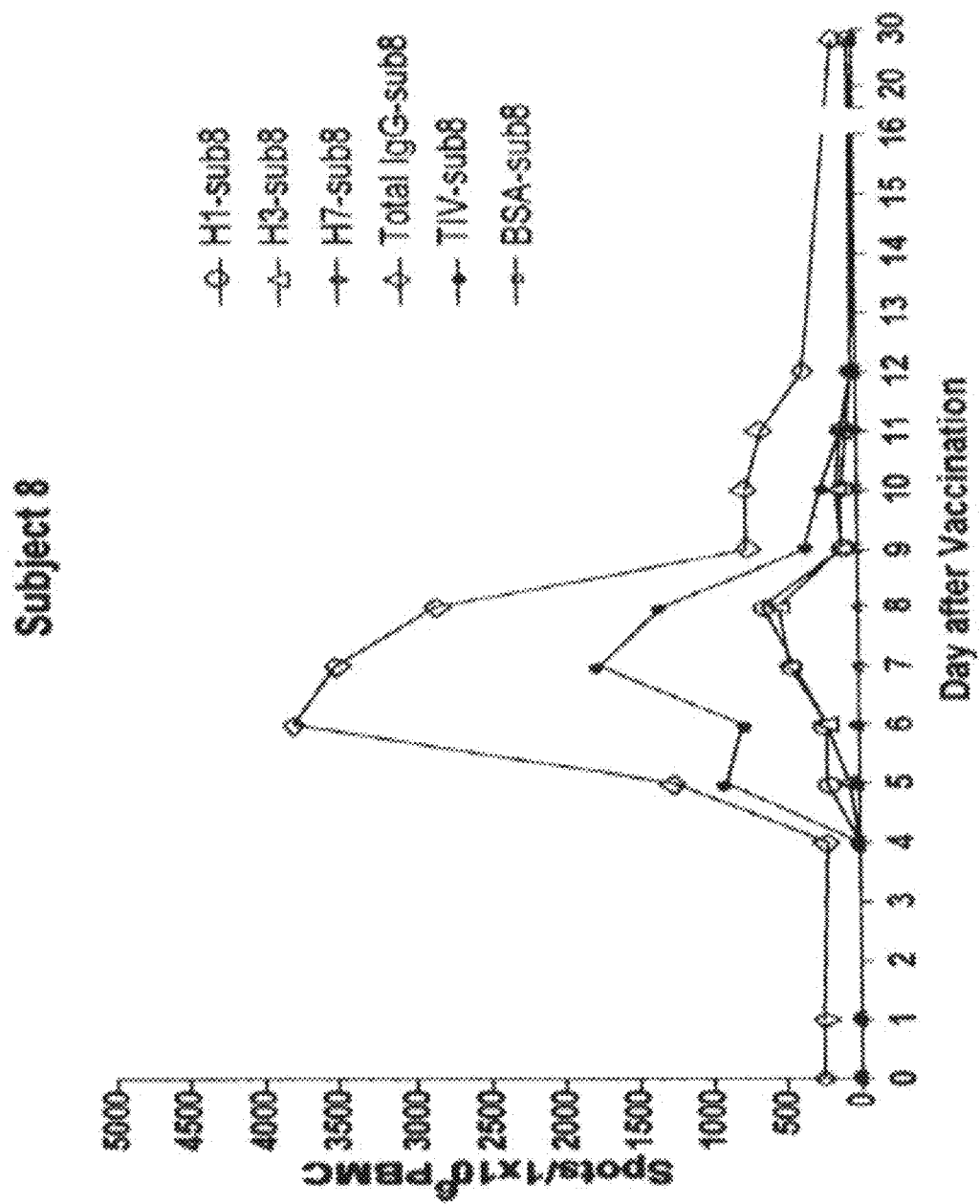

The antigen-specific ASC ex vivo in the blood after antigen exposure is short-lived approximately from day 5-15 after a single antigen dose (FIG. 5). These responses were very transient and very specific to the antigen of exposure. Thus making the presence of the antigen-specific ASC in the blood a very sensitive and very specific test to determine the antigen of exposure. The antigen-specific ASC in the blood were no longer present on day 28 post TIV.

However, as noted above, after single antigen exposure, antigen-specific ASC were seen in the blood directly ex vivo as early as day 5-15 (FIG. 6). FIG. 6 shows kinetics of 6 young healthy adult human subjects receiving influenza vaccine. Subjects with previous history of influenza vaccination (FIG. 6A, C, D) had lower peak TIV-specific ASC/million PBMC in the blood. Many subjects could recall a history of influenza infection however 2 of the 6 subjects could not recall a history in influenza infection (FIG. 6B, E). It is more likely these adult subjects had subclinical influenza infection. The antigen-specific ASC were very transient in these 6 subjects with variable peaks occurring differently for each subject and ranging from day 5-8. It is quite possible that previous history of flu vaccination resulted in the early rise in antigen-specific ASC responses indicating an early burst due to memory B cells as opposed to naive B cells. The peak or the magnitude of the rise can correlate with 4 week rise of HAI or antigen-specific antibody levels. Thus, the magnitude of the antigen-specific ASC in the blood can function as an early biomarker of humoral vaccine responses. The early or late peaks can also correlate with long-term antibody levels indicating differentiation to CD138$^+$ plasma cells.

Moreover, the antigen-specific ASC in the blood were specific to the antigen of exposure showing no cross-reactivity with unrelated antigens. Furthermore, non-influenza samples were tested showing that the ASC ELISPOT can work with any antigen to reveal a subjects antigen specific ASC. Examples shown herein include Tetanus, influenza vaccination, acute influenza and RSV infections.

For example, there was a massive increase in tetanus-specific and total IgG ASC in the blood directly ex vivo of a healthy human subject 7 days after tetanus vaccination. In the same individual, there was no RSV-specific (RSV F, Ga, Gb, Hepatitis B), or influenza-specific (H1, H3 wyoming, H3 wisconcin) ASC. Additionally, there were only very few TIV-specific responses. The few TIV-specific ASC can be due to cross-reactivity with tetanus, by-stander non-specific proliferation, or nonspecific background. The H7 (an irrelevant avian strain) and BSA were negative controls.

Antigen-specific ASC were also evaluated directly ex vivo during an acute Respiratory Syncytial Virus (RSV) Infection. There are 2 major subtypes of RSV as identified by the RSV G protein Ga and Gb. By the age of 2, nearly all children have had RSV infection and repeat infections are common in children and adults. As an adult, antibodies to both the Ga and Gb proteins are detected in nearly all healthy subjects. This human subject had RSV-per documented infection and RSV-specific F, Ga, and Gb ASC were detected in the blood directly ex vivo from day 5 and 12 of symptom onset. Again, this response was transient and by day 25 nearly all the antigen-specific ASC were not easily detectable. There were no TIV or influenza-specific ASC in the blood demonstrating specificity. The background ASC responses were zero.

A brisk expansion of total IgG ASC (5- to 10-fold from baseline) was observed after immunization with four different Ags (influenza, tetanus, hepatitis B, and HPV). Strikingly, in all cases, we readily detected significant frequencies of ASCs reactive with the corresponding vaccine but no responses above background levels to any of the other four Ags (FIG. 3). For example, increased influenza-specific ASCs after TIV are shown with undetectable ASCs to the unrelated Ags. Similar specificities were detected with ASCs against tetanus, hepatitis B, and HPV Ags although the magnitude of the responses was variable (FIG. 13). Tetanus responses were particularly striking as nearly all ASCs are Ag-specific accounting for 97% of the total IgG frequencies. Hepatitis B and HPV vaccination showed similar results but lower frequencies compared with those for influenza or tetanus. Importantly, the nonspecific bystander ASC responses in adults to universally exposed RSV protein are not detectable with influenza, tetanus, hepatitis B, and HPV vaccination. These data are representative of lack of bystander ASC responses to at least one of the nonspecific Ags in an additional nine and five patients receiving influenza or tetanus vaccine, respectively. The nonspecific RSV ASC frequencies during immunization were similar to asymptomatic responses (p=0.08). In addition, ASCs to these five Ags could not be detected in an asymptomatic healthy adult control (FIG. 13).

Additionally, disclosed herein is the ability to diagnose acute infections with RSV-specific ASC Elispots in the blood. RSV F specific ASC were measured in the blood directly ex vivo during acute RSV infection in 18 adult outpatients during the winter of 2007-2008. Each subject had multiple time points. The acute RSV infections were documented by RSV-per from nasopharyngeal swabs. RSV-F-specific ASC responses were detected in the blood as early as day 2 of symptom onset. In some of the subjects, by day 11 the RSV-F-specific ASC responses directly ex vivo had decreased. 17/18 subjects were identified with documented per-positive RSV infection by the RSV-F specific ASC responses ex vivo.

RSV F specific ASC were also evaluated in the blood directly ex vivo during acute RSV infection in 22 adult hospitalized patients during the winter of 2007-2008. Many subjects had multiple time points. The acute RSV infections were documented by RSV-per from nasopharyngeal swabs. RSV-F-specific ASC responses were detected in the blood as early as day 2 of symptom onset. By day 11 the Elispot responses were still positive. Many subjects were still positive by day 28 and 33 after symptom onset. Many of these subjects were still shedding virus on day 20 of symptom onset. 18/22 subjects were identified with documented per-positive RSV infection by the RSV-F specific ASC responses ex vivo. Subjects 20378, 20345, and 20386 may have been on high dose steroids or immunocompromised. However, subject 20445 with a low level RSV-per positive test actually had no RSV-F-specific ASC in the blood but had a very high influenza-specific ASC response. Repeat RSV-per testing demonstrated negative results indicating that the RSV-F-specific ASC Elispot is more specific than the RSV-per nasal swab. In fact, of the RSV per+ subjects, the RSV-specific ASC ELISPOTs correctly diagnosed 35/39. Additionally, the RSV-specific ASC Elispots identified one false positive subject. Thus the disclosed ASC ELISPOTs are at the minimum as accurate as per testing and do not have the draw back of having a potential false positive. In a second comparison with PCR, 74 for subjects (29 infected with Influenza) were assessed for viral exposure. PCR correctly identified 16 of the 29 exposed individuals. However, the ASC ELISPOT (MicroBspot) was able to correctly identify 20 of the 29 exposed individuals; i.e., a 38% improvement over the present gold standard.

Figure 9:
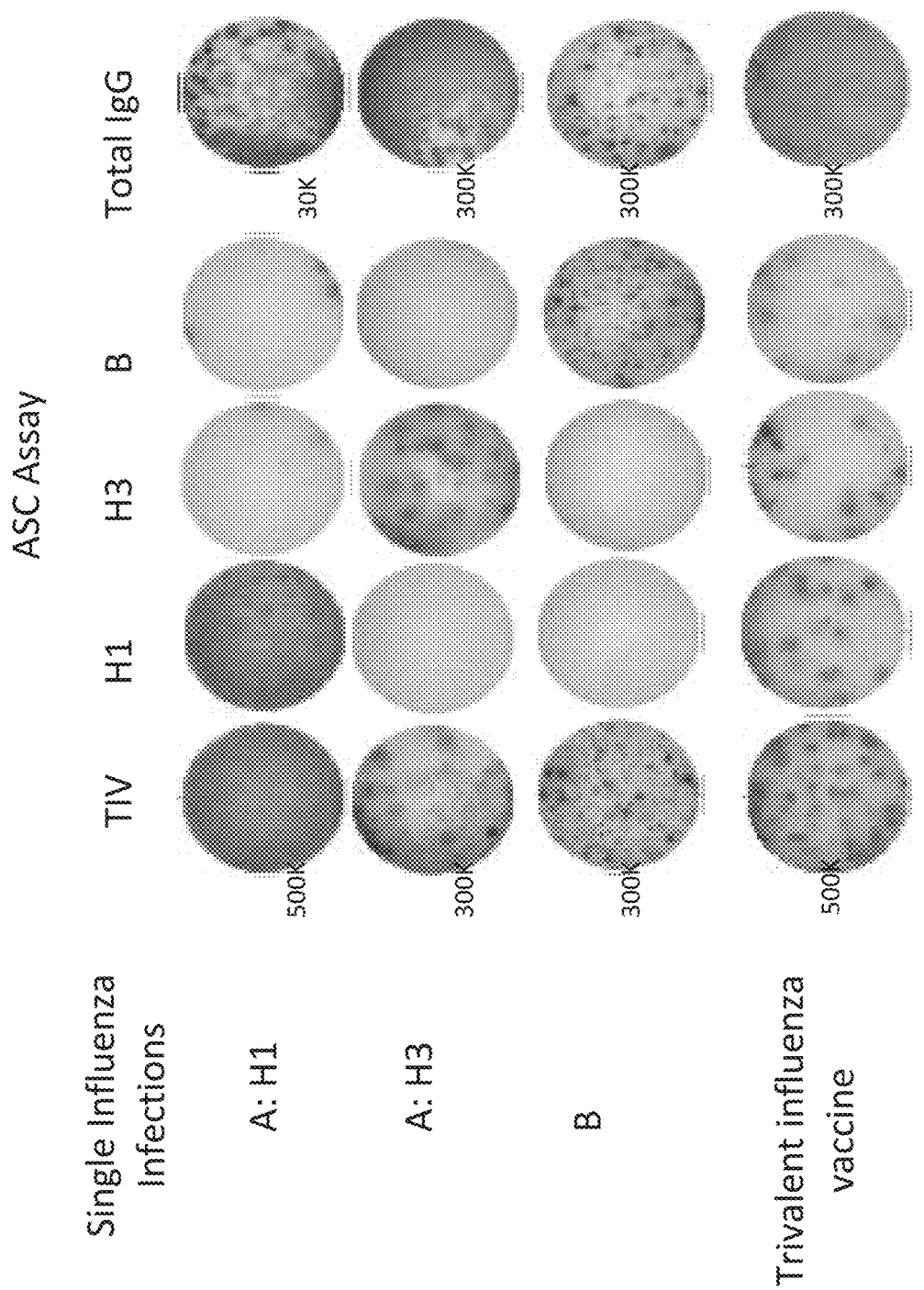
FIG. 9 shows the specificity of the microBspot™ assay is sensitive enout to distinguish between specific infections of Influenza. Patients with Influenza A (H1 or H3), Influenza B, or patients receiving a trivalent influenza vaccine were measured for specific antibodies.

Not only are the responses sufficiently specific to distinguish between viral and toxin ASC (Influenza and Tetanus) as well as different viral ASC (RSV and Influenza as well as RSV or Influenza and HepB or HPV) (FIG. 8), but the ASC are specific enough to distinguish between antigen strain exposure (FIG. 9). Antigen-specific ASC were also evaluated directly ex vivo after influenza vaccination and acute influenza infection. Again these antigen-specific ASC were transient in the blood after antigen-exposure. In the influenza vaccination, the vaccine-specific ASC were found ex vivo on day 7 after vaccination and could not be detected by day 35. Individuals exposed to Influenza A (H1 or H3); Influenza B; or having received a trivalent Influenza vaccine were analyzed for reactivity and specificity of ASC responses. The ASC ELISPOT correctly identified the specific strain of exposure with zero cross-reactivity between strains.

Additionally, in a subject with documented acute influenza A strain infection (Quikvue), influenza-specific ASC were found 6 days after symptom onset with decreasing numbers by day 8 and only a few spots detectable by day 28. The TIV-specific ASC responses was due to specificity directly to the current TIV HA strains, (A/Solomon Islands/3/2006 (H1N1), A/Wisconsin/67/2005 (H3N2), B/Malaysia/2506/2004) or due to cross-reactivity to one of these antigens.

Figure 7:
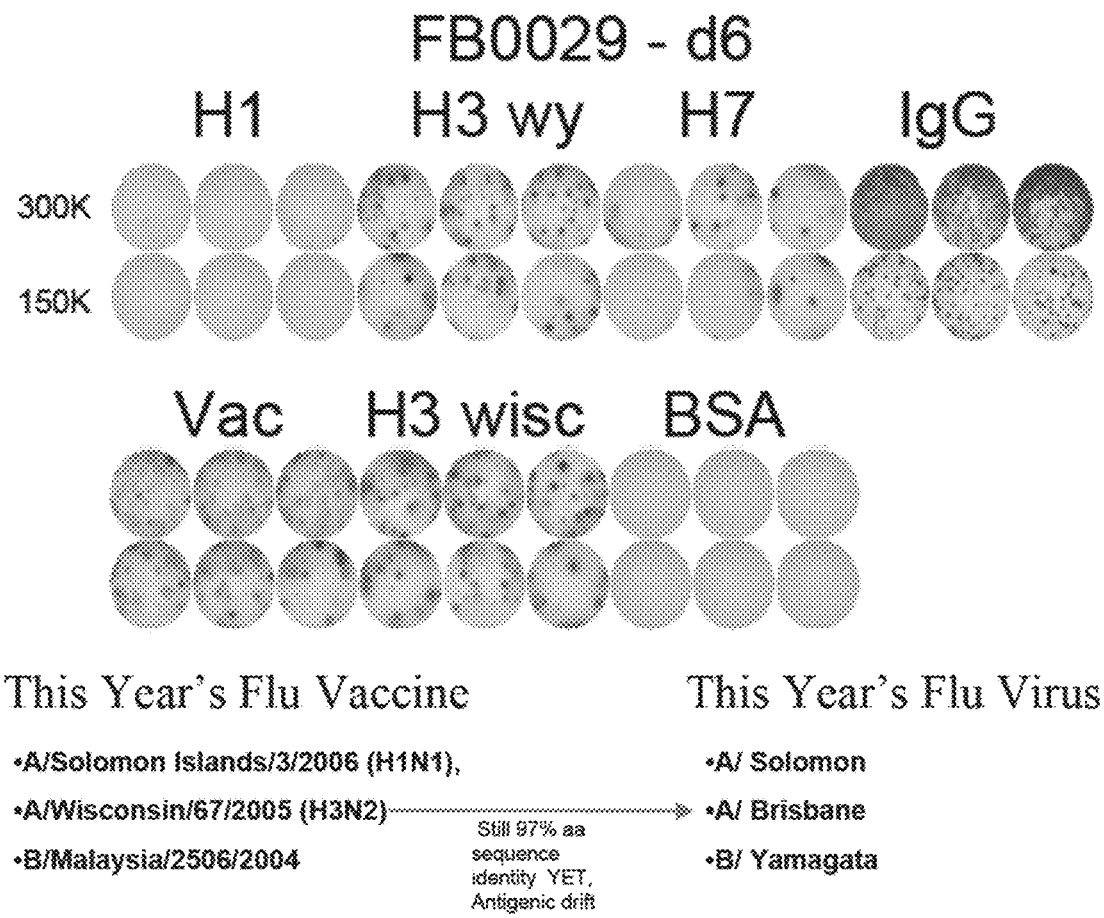
Figure 10:
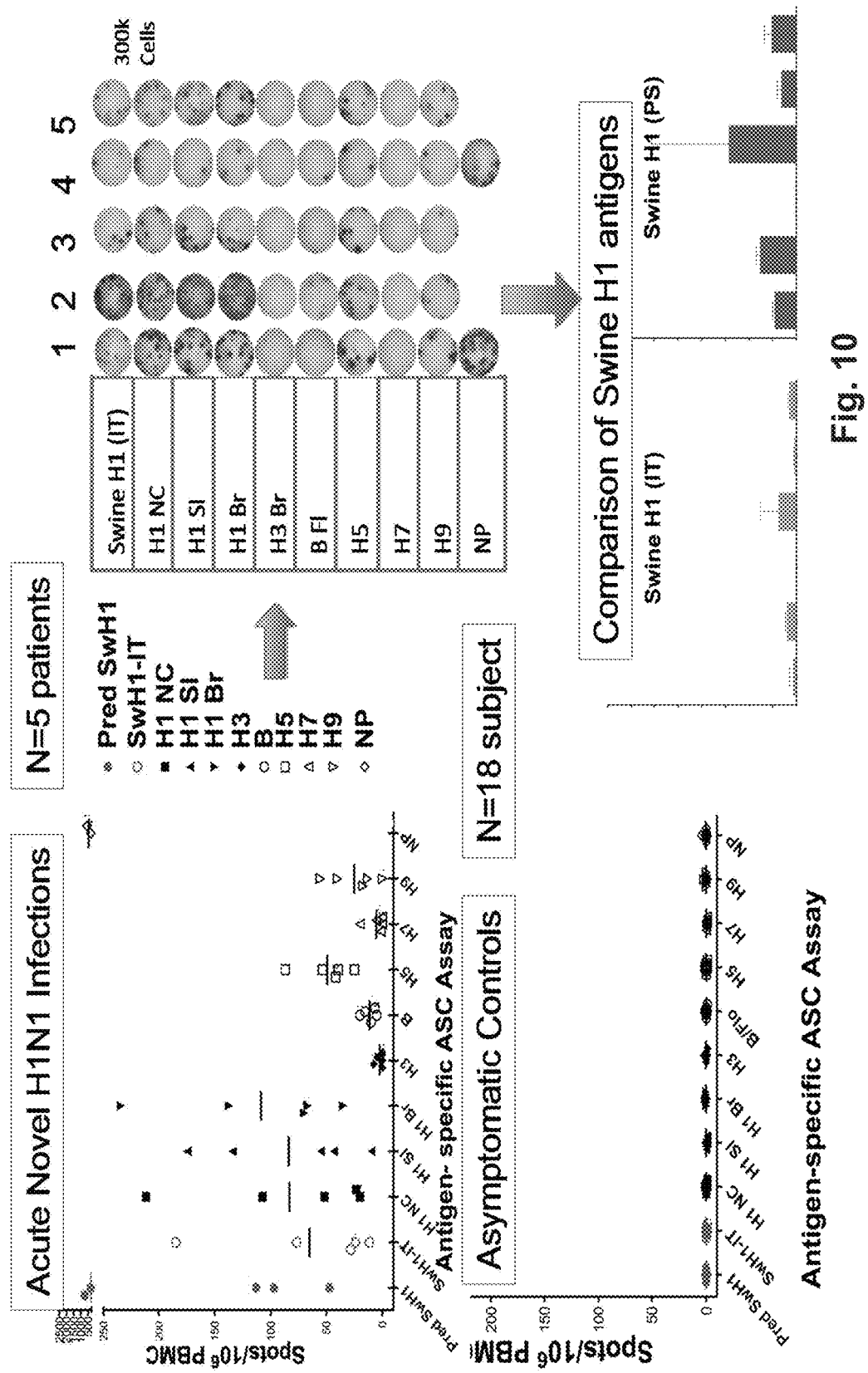
FIG. 10 shows that antigen-specific assays can be used to identify and distinguish acute influenza infections of different influenza strains including H1N1 *Swine H1), H1 NC, H1 S1, H1, Br, H3, B F1, H5, H7, H9, and NP. Assays show the number of spots per million PBMC and comparison of H1 antigens.

Antigen-specific ASC Elispots can further identify acute influenza infections of different influenza strains (FIGS. 7 and 10). The patient with acute influenza A infection probably had an H3 infection since H3 ASC elispots could only be detected ex vivo from the blood. H1-ASC responses were not detected 6, 8, or 28 days after symptom onset. The H3 Wyoming and Wisconsin H3 are very closely related. It is likely that this subject had infection with Influenza H3N2 A Brisbane since this subject received the influenza vaccine. Despite the antigenic drift between A/Wisconsin and A/Brisbane, cross-reactive epitopes were likely present. The isolated influenza A virus strain can be identified by sequence. These results were seen in two subjects with the same acute influenza A infection.

Traditionally ASC cells identified by flow cytometry are $CD19^+$ (or lo), $CD27^{hi}$, $CD38^{hi}$, $IgD^-$. These populations were identified by flow cytometry. The frequency of the plasmablasts as identify by flow cytometry is less than 50% of the population by total IgG ASC Elispots. The total IgG ASC and antigen-specific populations were derived from several populations (plasmablasts $CD27^{hi}$, $CD38^{hi}$ but $CD138^+$ and CD27 memory B cells). Multiple populations of $CD138^+$, $CD19^+$ B cell subsets were sorted from 200 mL of blood from a human donor 7 days post TIV. Populations were sorted and total IgG and TIV-specific ASC Elispots were performed.

Total IgG ASC Elispots were detected in the following populations in the blood 7 days post-TIV: $CD138^+$ cells, ASC (plasmablasts) $CD19^+$, $CD27^{hi}$, $CD38^{hi}$, $IgD^-$, and memory $CD19^+CD27^+$, $IgD^-$, with a few in the double negative $CD19^+CD27^-IgD^-$ B cell populations. No total IgG ASC Elispots were detected in the naïve or the unswitched memory populations. The antigen-specific TIV-specific ASC were found in the following populations: $CD138^+$ cells, ASC (plasmablasts) $CD19^+$, $CD27^{hi}$, $CD38^{hi}$, $IgD^-$, and memory $CD19^+CD27^+$, $IgD^-$, with a few in the double negative $CD19^+CD27^-IgD^-$ B cells (Table 1). Thus, the cell populations responsible for the antigen-specificity of ASC in the blood with vaccination include: blood plasma cells ($CD138^-$), plasmablasts ($CD19^+IgD^-$ $CD27^{hi}CD38^{hi}$), memory B cells ($CD19^+$, $IgD^-CD27^+$).

TABLE 1

Total IgG and TIV-specific ASC from Sorted populations 7 d post TIV.

| Sorted Populations | % Total IgG/sorted cell | Total IgG/10⁶ PBMC | % Fluvac/ sorted cell | Fluvac/ 10⁶ PBMC | Fluvac/ Total IgG |
|---|---|---|---|---|---|
| CD138⁺ | 1.32 | 546 | 0.21 | 88 | 0.16 |
| CD27ʰⁱCD38ʰⁱ | 2.04 | 746 | 0.97 | 353 | 0.48 |
| DN | 0.04 | 447 | 0.01 | 101 | 0.25 |

TABLE 1-continued

Total IgG and TIV-specific ASC from Sorted populations 7 d post TIV.

| Sorted Populations | % Total IgG/sorted cell | Total IgG/10$^6$ PBMC | % Fluvac/ sorted cell | Fluvac/ 10$^6$ PBMC | Fluvac/ Total IgG |
|---|---|---|---|---|---|
| Naive | 0.00 | 27 | 0.00 | 0 | 0 |
| Memory | 0.13 | 989 | 0.05 | 349 | 0.38 |
| Unswitched Memory | 0.01 (background) | 25 | 0.02 (background) | 37 (background) | 2 (unclear)? |
| Calculated TOTAL | | 2779 | | 928 | 0.33 |
| ACTUAL numbers from TOTAL PBMC | | 1500 ± 275 | | 1040 ± 204 | 0.69 |

Antigen-specific ASC were detectable in many healthy subjects not currently vaccinated or infected. All adult subjects had RSV infection multiple times. All adult subjects had clinical or subclinical influenza infection as adults. RSV-specific ASC can be detected in the human bone marrow from long-lived plasma cells. The influenza-specific ASC can also be found in healthy human bone marrow from long lived plasma cells.

These Antigen-specific ASC are very specific and sensitive. The same antigen-specific ASC was detected in bone marrow but not in blood of the same subject at day 0. Using this assay an increase in the TIV-specific ASC can be detected in the blood directly ex vivo after influenza vaccination. TIV-specific ASC could not be detected in the same subject in the blood at day 28 after vaccination. At week 17 after vaccination, the same frequency of TIV-specific per 1000 IgG producing CD138$^+$ cells were detected. Explanations for this include: (1) no increase in long-lived plasma cells post TIV; (2) equal rise of total IgG CD138$^+$ cells and flu-specific IgG producers; (3) sensitivity limits of the assay to detect minute differences in antigen-specific CD138$^+$ responses; (4) apoptosis and replacement of old TIV-specific CD138$^+$ ASC plasma cells in the bone marrow after vaccination with new immigrants; and/or (5) no new immigrant TIV-specific ASC into the marrow.

3. Example 3

MENSA as Measured by ASC Elispots is an Excellent Immunodiagnostic Approach

Prior to investing in a rapid clinically-based assay, evidence that this novel body fluid is a useful diagnostic test was needed. Therefore, these results were confirmed using human clinical samples in a common respiratory infection, RSV disease, by developing research-based RSV-specific ASC Elispot assays. A critical aspect of this assay included separation of the ASC from the plasma that was teaming with historical antibodies. These cells were given time to secrete antibodies (which were highly pathogen-specific during infection) on an RSV antigen-bound membrane. Thus only RSV-specific newly secreted antibodies were immediately captured and detected. The results showed that measurements of MENSA identified patients with >90% sensitivity and nearly 100% specificity who had PCR confirmed acute RSV infections.

This study was performed in both inpatients and outpatients or real-life scenarios at the time of initial clinical presentation. Thirty-nine patients with PCR confirmed RSV infections were enrolled, and this new diagnostic test identified 35/39 accurately at clinical presentation. In some patients, positive identification was made as early as the 2nd day of symptoms. This test provided results in real-time and not after the patient recovered which is often the case for most immune-based diagnostics. Unlike serum or plasma, MENSA by ASC Elispots appeared days earlier probably due to early appearance of the cells and the increased sensitivity 18. In conclusion, MENSA as a diagnostic is highly sensitive and specific as early as day 2 of illness and beyond.

4. Example 4

MENSA is Very Specific after Recent Vaccination and Infection

Indirect evidence indicated that non-specific memory B cells differentiate during vaccination and form circulating ASC. However, the data shown herein shows no evidence of bystander ASC responses after vaccinations (with antigens such as tetanus toxoid, hepatitis B surface antigen, and human papilloma virus VLPs). Influenza vaccination stringently induces abundant circulating ASCs specific for influenza proteins but does not expand ASC reacting with other pathogens either by cross-reactivity or by non-specific polyclonal activation of memory B cells against unrelated antigens. Also, circulating ASC present in 28 healthy adults in the absence of immunization do not contain detectable responses against influenza or any other major pathogens. This exquisite specificity holds true during acute respiratory viral infections such as RSV and influenza virus whereby false positive are minimized. Thus, the nearly 100% specificity that was found. In conclusion, ASC responsible for MENSA represent excellent biomarkers for diagnosis of a microbial infection due to the combination of several salient properties. First, the abundance of circulating antigen-specific ASC cells increases greater than 500-fold in the peripheral blood after vaccination or infection.

Figure 11:
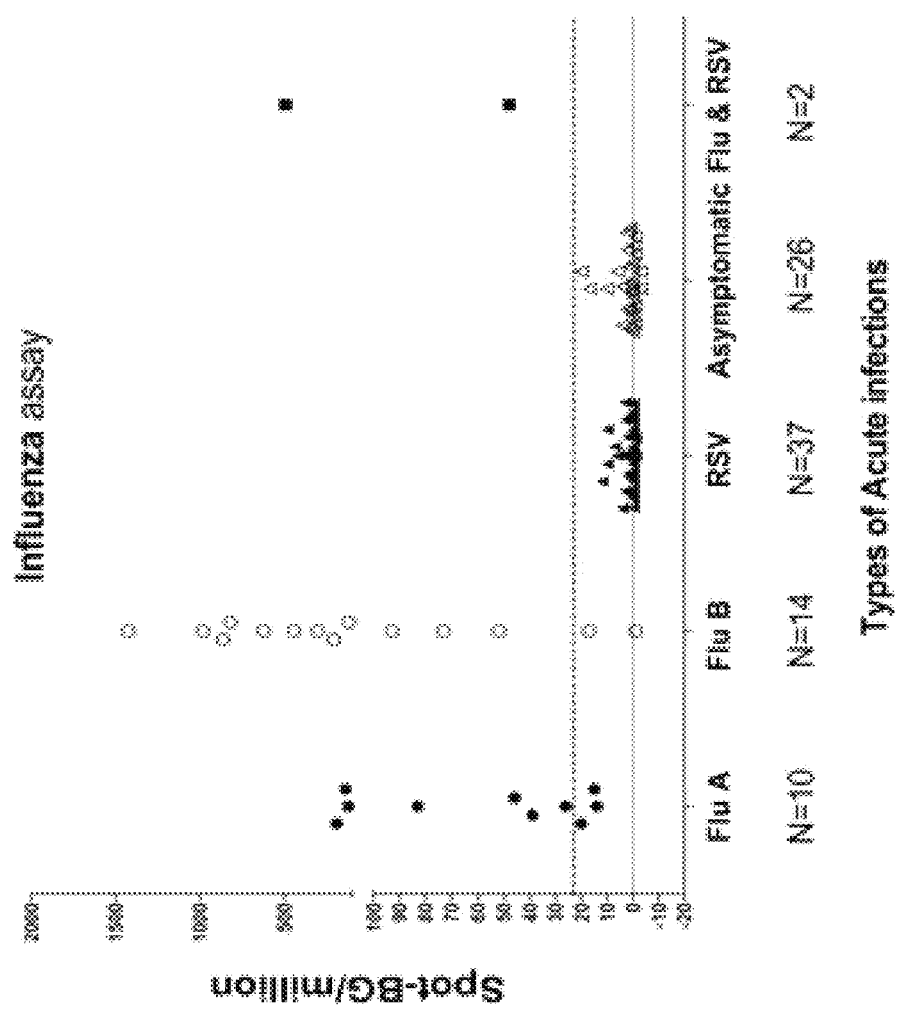
FIG. 11 shows Results of influenza (TIV+) ASC assays from frozen PBMCs are shown for patient groups with influenza A infection only, influenza B infection only, RSV infection only, dual (influenza B and RSV) infections, and asymptomatic controls. The upper horizontal line represents the cut-off for a positive ASC assay calculated as the mean+4SD.

Second which is of foremost importance, these cells secrete antibodies with amazing specificity for the microbe of recent exposure. Combined, the absence of baseline responses (ensuring very low experimental noise in the assay) and lack of bystander responses represent crucial elements for this diagnostic assay. Dual specificity means dual infections. A powerful illustration of the diagnostic potential of MENSA is provided by its ability to detect simultaneous infections with different organisms. MENSA specific for both an RSV and influenza on day 8 from one patient recruited with confirmed RSV infection by PCR 1. These findings suggested two possibilities: a unique massive bystander response or a simultaneous RSV and influenza virus infection. The latter was confirmed when repeat nasopharyngeal PCR tests revealed a co-infection with influenza virus confirming the ASC specificities. (additional cases are shown in FIG. 11). In conclusion, dual ASC specificities exemplify true co-infections.

5. Example 5

Circulating ASCs are Special and Characteristically Different from Long-Lived Plasma Cells.

During infection or vaccination, naïve or memory B cells (in different frequencies for primary versus recall responses), undergo massive proliferation and differentiation into ASCs in the draining lymph nodes then explode into the blood as they migrate to other tissue sites such as the bone marrow for permanent residence. The relationship between circulating ASCs and long-lived plasma cells is not well understood although many models have been proposed. Focus was not on the immune models but exploited the differences of these two cell types by their phenotype, kinetics, location, and secreted antibody specificity for the development of this new diagnostic test.

Circulating ASCs are Actively Proliferating in Response to Recent Antigenic Stimulation whereas Long-Lived Plasma Cells are Resting Cells.

Circulating ASCs represent the plasmablast population actively responding to an ongoing antigenic insult whereas resident bone marrow long-lived plasma cells are responsible for the historical antibodies found in plasma. Studies demonstrate that, while careful multicolor flow cytometry can identify several distinct subsets of circulating ASC populations, the majority of these cells can be captured within the CD19+, CD27hi, CD38hi population containing >90% of recently proliferated cells as indicated by the almost universal expression of the nuclear proliferation antigen Ki67. In contrast, the majority of human bone marrow plasma cells are CD138+ CD27hi CD38hi with less than 5% expressing Ki67 indicating many are non-dividing.

In the following experiments (unless specified), ASCs are separated from plasma using traditional Ficoll density centrifugation of peripheral blood mononuclear cells (PBMC) which contain the ASCs. MENSA is predicated on the principle of antigen specificity of contemporary antibodies newly generated in real time during acute infection. This is in contra-distinction to pre-existing plasma antibodies which denote simply the presence of long-lived bone marrow plasma cells generated at the time of prior infections and which are therefore ineffectual if not misleading in the context of acute infection. Of note, this spontaneous antibody secretion assay does not measure resting memory B cells since memory B cells do not secrete antibodies spontaneously but require a prerequisite 4-6 days of in vitro proliferation and differentiation to secrete antibodies.

Specificity of MENSA with Influenza A & B Infections Versus Vaccination.

Two major types of influenza virus infect humans: types A and B and the envelope glycoproteins comprise of hemagglutinin (HA) and neuraminidase (NA). In type A viruses, a minimum of 15 highly divergent, antigenically distinct HAs (H1 to H15) and 9 distinct NAs (N1 to N9) have been described. Influenza A viruses are further divided into subtypes based on the HA and NA combinations, e.g., H1N1 or H3N2. While cross-neutralizing antibodies between influenza subtypes (hetero-subtypic immunity), have been described, they are difficult to detect in plasma or serum due to inability to distinguish between "old vs. new" antibody responses in the plasma. MENSA measured by ASC ELipsots during influenza virus infections are highly specific for the ONLY the circulating strain with very little cross-reactivity between Influenza A:H1N1, A:H3N2, and B infections (FIG. 9). In contrast, in patients immunized with trivalent influenza vaccine (TIV), MENSA show specificity to all 3 HA's contained in the vaccine. Collectively, the results provide evidence that MENSA is highly specific for the HA antigen expressed by the offending strain hereby increasing its diagnostic value.

Specificity of MENSA in Patients with Non-RSV Infections.

To test the specificity of MENSA for non-RSV infections, in an additional pilot study, 68 patients with community acquired pneumonia prior were enrolled to the RSV season at Rochester General Hospital, Rochester N.Y. in the fall of 2009. One subject was found to be positive by RT-PCR for RSV by nasal swab. MENSA was negative in 67 patients and found to be positive in the one confirmed RTPCR subject. Using PCR as the gold standard, sensitivity of 93%, specificity of 100%, positive predictive value of 100% and a negative predictive value of 96% was found in MENSA for RSV diagnostics.

Diagnosis of influenza infection with MENSA from frozen blood samples. Given the specificity of the assay shown above, an initial study was performed to test its ability to diagnose influenza infection. This first study was performed on available frozen PBMC samples from 24 patients with confirmed influenza infection in 2006. As shown in FIG. 11, MENSA specificity performed with the corresponding influenza HA proteins: A/H1/Solomon Islands, A/H3/Wisconsin, and B/Malaysia HA antigens were able to diagnose 18/24 confirmed patients. Interestingly, 2 subjects demonstrated a concurrent RSV and influenza infection confirmed by both RSV and influenza B PCR and/or paired serology. Therefore, sensitivity and specificity of the influenza assay was 81% and 100% respectively when performed from frozen PBMC. This is a remarkable result given the well-known sensitivity of ASC to freezing-thawing manipulations results in significant loss of overall cell numbers. The study, however, was enabled by the previous demonstration that the relative ratios of antigen-specific ASC to total PBMCs are preserved with frozen PBMCs in post-vaccination blood. Therefore, the sensitivity of the influenza assay is approximately that of the RSV assay when fresh samples are used. Collectively, it is demonstrated herein that this novel approach can detect antigen or PCR confirmed influenza virus infections with good sensitivity and specificity.

Increasing Sensitivity with a Combined IgG, IgA, and IgM Detection to Diagnose 2009 Pandemic Influenza Infections.

Building on the IgG detection, IgM and IgA antibodies were added since IgM responses indicate newly recruited B cells against specific epitopes restricted to the circulating strain and IgA responses are a major arm of the immune response to mucosal inoculation (main route of influenza infection). Accordingly, this study was performed with both IgG and IgA ASC in adult patients with respiratory illness at initial presentation (days 2-11 after symptom onset) during the fall/winter of 2009 pandemic season in Rochester, N.Y. The following criteria was used to validate MENSA using the influenza ASC Elispot assay: (a) with a range of 30,000-1,000,000 PBMC per well, a positive control with total IgG, IgA, or IgM ASC >10 spots/well; (b) negative control (or BSA) <3 spots/well, (c) influenza-ASC wells >5 spots/well and responses>mean+4 SD of the healthy asymptomatic group. A positive cut-off mean+4SD above 10 healthy asymptomatic controls was used because this includes >99.99% of the control subjects. 74 adult hospitalized and outpatient adults (21 to 85 years) were enrolled and measured influenza-specific IgG, IgA & IgM ASCs. From 74 patients, 27 positive cases were identified by either PCR or by the ASC Elispots. Nine were positive by both methods; 7 were detected by PCR alone, and 11 additional patients were positive by the assay. It is notable that 11 additional or 11/27 (41%) more cases were detected with MENSA thereby establishing its diagnostic potential.

Kinetics of Antibody Secretion from ASC.

Antibody secretion by the circulating ASC can be detected within one hour. The results show that in a patient 7 days after tetanus toxoid vaccination, tetanus specific ASC are easily detected by ASC Elispots within one hour. Similar numbers of ASC elispots are found after 1, 2, 3, 4, 6 and 18 hours of antibody elaboration or secretion. Numbers of spots may actually decrease with increased time due to coalescing Elispots as individual spots grow with time as more antibodies are secreted into its surroundings. This result demonstrates that antibody secretion is ongoing in the blood and continues ex vivo from the subject the moment the blood is withdrawn from the patient. At present, incubation time is typically about 6-18 hours, but this time can be substantially reduced since antibody secretion plateaus after 4-6 hours ex vivo. The data indicate that one cell secretes 10 pg per hour or 9,000-12,000 IgG molecules/sec. Antibody production by ASCs has been estimated at about 10,000 antibody molecules per second or about $3\times10^7$ antibody molecules per ASC per hour, or about 10 picograms/hr/ASC which confirms the measurements. From the calculations, in one mL of volume, a single ASC produce enough antibody molecules to reach about $1\times10^{-12}$ M which is near the limits of sensitivity of the best commercial immunoassays. However, the Elispot assay indicates that detection of >5 spots or cells are needed for a conclusive positive result. Thus, if antibodies are collected in 100 uL (concentrated 10 fold), the lower limit of detection is approximately 0.5 ng/mL/h from only 0.3 mL of blood which are well-within the limits of detection of currently available immunoassays such as chemiluminescence (with reliability within pg/mL ($10^{-12}$ M)). Furthermore, hospital modular analyzer easily detect protein concentrations such as cardiac troponins in less than 0.01 ng/mL routinely to diagnose myocardial infarctions or "heart attacks" illustrating that immunoassays for pathogen-specific antibodies from MENSA that can be placed on existing hospital analyzers. Importantly, in a majority of the samples, the frequency of ASC is much higher than 5. Typically it is 10-500 ASC from 0.3 mL of blood. Thus, starting with larger blood volumes 1-10 mL, MENSA yield nanograms or micrograms or potentially enormous amounts of pathogen-specific antibodies.

Determinants of the appropriate antigen or combination of antigens for each pathogen for MENSA to diagnose infections are not trivial. Many pathogen-specific ASC Elispots have been developed as potential diagnostic antigens for acute infections. A partial list of the specific microbes includes: influenza virus (including avian H5N1 and 2009 pandemic H1N1) and RSV, *Streptococcus pneumoniae*, *Staphylococcus aureus*, hepatitis B virus, and human papilloma virus, *Meningococcus*, and *C. difficile* toxins. These assays can easily be converted to an existing ELISA or chemiluminescence immunoassay format to measure MENSA in an automated fashion.

6. Example 6

Approximately 1,000 adult patients are enrolled with ILI in this study and 200 household contacts. MENSA is isolated and detection of influenza-specific antibodies is performed by ELISA methods as well as ASC ELispots. In addition, MENSA and ASC ELispots are compared to the standard reference assays of PCR and rapid antigen (by one of the 10 FDA approved). The current influenza IgG, IgA and IgM ELISA detection is performed from MENSA using the following antigens: annual trivalent vaccine (TIV); NP, HA (H1, H3 and B) for that season and/or any new mutated pandemic strains. IgG, IgA, and IgM ASC Elispots are also performed for the above-mentioned antigens. NP antigens are used as a highly conserved protein that is not be susceptible to re-assortments and new mutations. Different HA's are used to identify individual influenza virus types and subtypes. Serology can also be measured.

A positive influenza infection is defined by a positive result by one of 3 reference assays (PCR, rapid antigen, or serology). Sensitivity of MENSA by ASC Elispots is determined at the initial time (further divided by days) and collectively at all time points. It is possible that PCR (compared to MENSA by Elispot assays) may have higher sensitivity early (first 2 days after symptom onset); however, MENSA outperforms PCR after day 3 and for overall time-points the results shown herein that most patients present after day 2 of symptoms. Thus some patients may be negative by PCR and positive by MENSA. Multivariate analysis using demographic and clinical data can be performed to determine if there are confounding factors that may influence the results.

Only the subjects with influenza have positive MENSA influenza antigens, and those with respiratory illness from other etiologies are negative. Adults with shorter duration of viral shedding are positive by ASC Elispot assay since challenge studies found that maximal shedding often occurs one day prior to symptom onset. The size of this group establishes the complementary value of the assay over current PCR gold standards. PCR may outperform MENSA in patients prior to the development of symptoms since viral shedding peaks prior to symptoms. However, the subclinical patients are positive by MENSA compared to PCR or antigen tests.

The current detection of the MENSA fluid include only IgG isotype antibodies, detection with other isotypes such as IgA and IgM can increase the sensitivity since mucosal infections generate an abundant of IgA antibodies and ASC that secrete IgA atnibodies. Using a combination of detection of both IgA and IgG (top panel, FIG. 12), patients were detected with the 2009 H1N1 pandemic influenza virus infection. The results were also notable regarding the ability of the ASC assay to detect cross-reactive epitopes in the majority of patients as illustrated in FIG. 12 by the co-existence of TIV (09-10), H1 Brisbane, and H1 California IgG and IgA ASC responses in a representative patient with PCR confirmed 2009 pandemic infection. In sharp contrast, IgM ASC responses were noted only to the H1 California and not to the seasonal H1 presumably reflecting a primary response generated against novel epitopes present in the pandemic strain. In conclusion, detection with different antibody epitopes can increase sensitivity.

Cross-reactivity of newly synthesized antibody using the ASC Elispot assayduring 2009 H1N1 influenza pandemic. During the initial outbreak of the 2009 H1N1 pandemic, acute H1N1 pandemic infections were correctly identified with the ASC assay. Having had in place Institutional Research Protocols to recruit patients with influenza infections since 2004, 5 patients were recruited with influenza-like-illness within one week of the outbreak. With the knowledge that the virus was of an influenza A H1N1, an array of the following influenza antigens was designed at the end of April of 2009 and measured newly synthesized antibodies from the fresh (not frozen) circulating ASC: H1 California 2009, H1 New Caledonia, H1 Solomon Islands, H1 Brisbane, H3 Brisbane, H5 '04 Vietnam, H7, H9 and NPA with negative controls that included RSV F protein and BSA. The new 2009 pandemic strain had cross-reactive epitopes to the seasonal H1N1 strains and as expected the virus generated ASC to the conserved NP proteins. It also had albeit low frequencies to H5 and H9 which may be due to the cross-reactive epitopes to the HA2 stalk. Little cross-reactivity to H3 and H7 were found which was not surprising since H3 and H7 are in phylogenetic group 2. No ASC were detected to RSV and BSA and eighteen asymptomatic subjects had no detectable influenza, RSV or BSA specific ASC responses.

What is claimed is:

1. An analytical matrix comprising media elaborated with newly synthesized antibodies (MENSA) from recently proliferated antibody secreting cells (ASC) circulating in the blood; wherein the analytical matrix comprises at least a $10^6$ or $10^7$-fold reduction of contaminating pre-existing plasma antibodies relative to whole blood, plasma, or peripheral blood mononuclear cells (PBMC).

2. The analytical matrix of claim 1, wherein the MENSA is cell free.

3. The analytical matrix of claim 1, wherein the MENSA is free from assay interferences, wherein the assay interferences comprise pharmaceutical agents, lipemia, icterus, bile salts, hemoglobin, heterophilic antibodies, autoimmune antibodies, vitamins, antioxidants, or nutritional supplements.

4. A method of producing an analytical matrix comprising MENSA the method comprising obtaining whole blood or PBMC from a subject separating plasma from the whole blood or PBMC to produce separated cells; isolating newly proliferated ASC from the separated cells; washing the newly proliferated ASC; and incubating the washed newly proliferated ASC in a media that supports maintenance of ASC and antibody secretion to thereby produce the MENSA; wherein the the analytical matrix comprises at least a $10^6$ or $10^7$-fold reduction of contaminating pre-existing plasma antibodies relative to whole blood, plasma, or PBMC.

5. The method of claim 4, wherein the newly proliferated ASC are separated and isolated from the plasma via ficoll gradient separation or elutriation.

6. The method of claim 4, wherein the newly proliferated ASC are separated and isolated from the separated cells via magnetic bead sorting or fluorescence acquired cell sorting (FACS).

7. The method of claim 6, wherein newly proliferated ASC are separated and isolated from the separated cells through use of antibodies specific for one or more cell surface markers comprising CD38, CD27, CD19, CD138, IgD, and Ki67.

* * * * *